(12) United States Patent
Tallon et al.

(10) Patent No.: US 10,233,276 B2
(45) Date of Patent: Mar. 19, 2019

(54) VINYL LACTAM-DERIVED POLYMERS, COMPOSITIONS THEREOF HAVING ENHANCED WATER-RESISTANCE, AND METHODS OF USE THEREOF

(71) Applicant: ISP Investments LLC, Wilmington, DE (US)

(72) Inventors: Michael A. Tallon, Aberdeen, NJ (US); Mousumi Ghosh, Elmwood Park, NJ (US); Krishnamurthy Nacharaju, Hilliard, OH (US); Hani M. Fares, Somerset, NJ (US); Donald I Prettypaul, Englewood, NJ (US); Osama M. Musa, Bedminster, NJ (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 15/301,429

(22) PCT Filed: Mar. 30, 2015

(86) PCT No.: PCT/US2015/023347
§ 371 (c)(1),
(2) Date: Oct. 3, 2016

(87) PCT Pub. No.: WO2015/153461
PCT Pub. Date: Oct. 8, 2015

(65) Prior Publication Data
US 2017/0174809 A1   Jun. 22, 2017

Related U.S. Application Data

(60) Provisional application No. 61/973,580, filed on Apr. 1, 2014.

(51) Int. Cl.
| | |
|---|---|
| *A61K 47/34* | (2017.01) |
| *C08F 226/06* | (2006.01) |
| *C08F 226/10* | (2006.01) |
| *C08F 220/18* | (2006.01) |
| *C08F 226/08* | (2006.01) |
| *A61Q 17/04* | (2006.01) |
| *A61K 8/81* | (2006.01) |

(52) U.S. Cl.
CPC ............ *C08F 226/06* (2013.01); *A61K 8/817* (2013.01); *A61K 47/34* (2013.01); *A61Q 17/04* (2013.01); *C08F 220/18* (2013.01); *C08F 226/08* (2013.01); *C08F 226/10* (2013.01)

(58) Field of Classification Search
CPC .... C08F 226/06; C08F 226/08; C08F 226/10; A61K 47/34
See application file for complete search history.

(56) References Cited

U.S. PATENT DOCUMENTS

| | | | | |
|---|---|---|---|---|
| 3,725,122 | A * | 4/1973 | Reinhard | C08F 220/18 428/355 AC |
| 4,137,392 | A * | 1/1979 | Gross | C08F 220/12 428/463 |
| 4,510,302 | A * | 4/1985 | Kolb | C09B 67/006 428/473 |
| 4,701,509 | A * | 10/1987 | Sun | A61L 15/58 526/264 |

(Continued)

OTHER PUBLICATIONS

Thermal Transitions of Homopolymers Downloaded from https://www.sigmaaldrich.com/content/dam/sigma-aldrich/docs/Aldrich/General_Information/thermal_transitions_of_homopolymers.pdf(Sep. 27, 2017).*
Polymer Properties database downloaded from http://polymerdatabase.com/polymer%20physics/Polymer%20Tg.html (Sep. 27, 2017).*
International Search Report, PCT/US2015/023347 published on Oct. 8, 2015.

*Primary Examiner* — Irina S Zemel
*Assistant Examiner* — Jeffrey S Lenihan
(74) *Attorney, Agent, or Firm* — William J. Davis; Nathalie Tietcheu

(57) ABSTRACT

The invention provides polymers comprising repeating units derived from (a) from 16% by weight to about 35% by weight of said polymer of at least one N-vinyl lactam monomer; (b) at least one monomer selected from the group consisting of functionalized and unfunctionalized $C_1$-$C_6$ alkyl (meth)acrylates, $C_1$-$C_6$ alkyl (meth)acrylamides and combinations thereof; and (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein the polymer has a glass transition temperature of greater than about 45° C. The invention further provides various compositions, such as, personal care, sun care, coatings, and pharmaceutical compositions comprising the polymers described herein. The invention furthermore provides water-resistant sun care compositions comprising the polymers described herein. Subscripts x, y and z are described herein. (Formula (I))

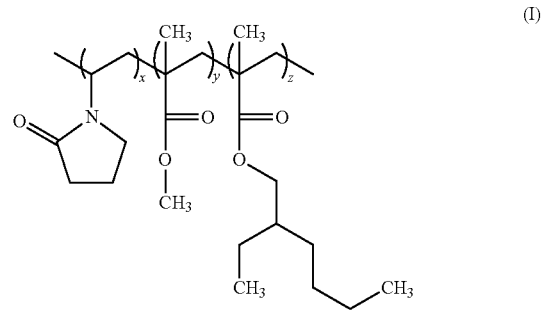

8 Claims, 5 Drawing Sheets

(56) References Cited

U.S. PATENT DOCUMENTS

| | | |
|---|---|---|
| 6,294,615 B1 | 9/2001 | Higashino et al. |
| 6,342,570 B1 | 1/2002 | Bothe et al. |
| 6,686,425 B2 | 2/2004 | Wigdorski et al. |
| 2002/0185222 A1* | 12/2002 | Wigdorski ............... B32B 15/04 156/306.6 |
| 2008/0220046 A1* | 9/2008 | Cheng .................... A61L 27/34 424/426 |
| 2013/0261268 A1 | 10/2013 | Hood et al. |
| 2015/0174042 A1* | 6/2015 | Leibler ................ A61K 8/8152 424/59 |

\* cited by examiner

Study of Percent Water Resistance of Various Polymers in Sun Care Emulsion I

Study of Percent Water Resistance of Various Polymers in Sunscreen Emulsion II

Study of Percent Water Resistance of Various Polymers in Sunscreen Emulsion III

Water Resistance Test Method

VINYL LACTAM-DERIVED POLYMERS, COMPOSITIONS THEREOF HAVING ENHANCED WATER-RESISTANCE, AND METHODS OF USE THEREOF

FIELD OF THE INVENTION

The invention provides vinyl lactam-derived polymers. The invention further provides compositions comprising the vinyl lactam-derived polymers. The invention furthermore provides personal care compositions, such as water-resistant sun care compositions comprising the vinyl lactam-derived polymers, and methods of use thereof.

DESCRIPTION OF RELATED ART

Aging skin is the result of more than just chronological age. Skin is exposed to various environmental stresses, such as ultraviolet (UV) rays, which cause free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical which may attack adjacent fatty acids to generate new carbon radicals. This process can lead to a chain reaction producing lipid peroxidation products. Damage to the cell membrane can result in loss of cell permeability, increased intercellular ionic concentration and/or decreased ability to excrete or detoxify waste products. The end result is a loss of elasticity of the skin and the appearance of wrinkles leading to premature ageing of the skin. This process is commonly referred to as photo-aging.

One of the requirements of commercial sun care compositions is to possess water-resistance properties in order to inhibit the protective composition from being easily removed from a keratinous substrate surface by sweat and exposure to water.

U.S. Pat. No. 4,978,527 teaches film-forming emulsion containing iodine and methods of use. The film-forming emulsion comprises: (a) a substantially water resistant film-forming copolymer phase comprising A, B and C monomers wherein A is a "soft" monomer wherein the corresponding homopolymer has a glass transition temperature (Tg) of less than about $-15°$ C., and is present as about 15 to 80% of the total weight of all monomers in the copolymer, B is a "hard" monomer wherein the corresponding homopolymer has a Tg of more than about $-5°$ C., and is present as about 20 to 70% of the total weight of all monomers in the copolymer, and C is a monomer capable of complexing iodine and delivering it to the skin and is present as about 1 to 15% of the total weight of all monomers in the copolymer; (b) about 0.05 to 15% of iodine based on total emulsion weight; (c) an effective amount of an emulsifying agent; and (d) about 30 to 95% by weight of water.

U.S. Pat. No. 4,584,192 teaches a film-forming composition containing an antimicrobial agent and methods of use. The film-forming composition comprises (a) a film-forming copolymer consisting essentially of copolymerized A, B, and C monomers as follows: A is a monomeric acrylic or methacrylic acid ester of an alkyl alcohol containing a single hydroxyl, the alcohol being further described as having from 2 to about 14 carbon atoms when the A monomer is an acrylic acid ester, and about 7 to 18 carbon atoms when the A monomer is a methacrylic acid ester, the amount by weight of A monomer being about 15 to 80% of the total weight of all monomers in the copolymer; B is a monomeric methacrylic acid ester of an alkyl alcohol containing a single hydroxyl, the alcohol being further described as having from 1 to about 6 carbon atoms, the amount by weight of B monomer being about 20 to 70% of the total weight of all monomers in the copolymer; and C is an N-vinyl lactam, the amount by weight of which being about 1 to 15% of the total weight of all monomers in the copolymer; (b) an effective amount of a broad spectrum antimicrobial agent; the composition being dermatologically-acceptable, and, when applied to skin from a fugitive solvent, being capable of forming a clear, substantially fluid-resistant, substantially tack-free, flexible film which adheres to skin and releases the antimicrobial agent to skin.

U.S. Pat. No. 7,745,505 teaches a UV-curable hot melt pressure sensitive adhesive comprising (a) from about 70 to about 95 parts by weight of methyl acrylate, methyl methacrylate, n-butyl acrylate, 2-ethylhexyl acrylate, and/or isooctyl acrylate, (b) 0 to about 30 parts by weight of hydroxyethyl acrylate and/or hydroxypropyl acrylate, (c) 0 to about 20 parts by weight of acrylic acid or maleic anhydride, (d) 0 to about 30 parts by weight of 1-vinyl-2-pyrrolidinone (NVP), t-octyl acrylamide, 2-(tert-butylamino)ethyl methacrylate (t-BAEM), acrylamide, glycidyl methacrylate, 3-Isopropenyl-α, α-dimethylbenzyl isocyanate (m-TMI®), and (e) from about 0.01 to about 15 parts by weight of a photoinitiator.

US published patent application 2008/0138300 teaches a cosmetic composition comprising, in a cosmetically acceptable medium: at least one acrylic polymer resulting from the copolymerization of: a) at least one monomer A chosen from esters derived from the reaction of (meth)acrylic acid with at least one monoalcohol comprising from 2 to 20 carbon atoms, b) at least one monomer B chosen from esters derived from the reaction of methacrylic acid with at least one monoalcohol comprising from 1 to 10 carbon atoms, and c) at least one monomer C chosen from N-vinyllactams and derivatives thereof, and at least one organic solvent phase comprising at least one first organic solvent, wherein the at least one organic solvent phase comprises less than or equal to 15% by weight of solvents chosen from lower monoalcohols comprising from 1 to 5 carbon atoms and $C_3$-$C_4$ ketones, relative to the total weight of the composition. Advantageously, the monomer C is present in a numerical proportion ranging from 1% to 15% and better still from 5% to 15% relative to the total number of monomers in the polymer.

US published patent application 2010/0282409 teaches an antimicrobial composition comprising: a) a $C_2$-$C_5$ lower alcohol present in an amount of at least 35 wt-%; b) a hydrophobic polymer soluble or dispersible in the lower alcohol; c) an emollient ester; and d) a cationic antimicrobial agent; wherein the antimicrobial composition is free of surfactants with an HLB greater than 6; and wherein the antimicrobial composition is essentially free of hydrophilic polymers.

We have found that polymers according to the invention provide, among many other benefits, the important benefits of enhanced water-resistance and good skin feel. The polymers may be formulated into a wide variety of compositions for many important applications, non-limiting examples of which include personal care, sun care, coatings, agricultural, and pharmaceuticals.

SUMMARY

In a first aspect, the invention provides a polymer comprising repeating units derived from (a) from 16% by weight to about 35% by weight of said polymer of at least one N-vinyl lactam monomer; (b) at least one monomer selected from the group consisting of functionalized and unfunctionalized $C_1$-$C_6$ alkyl (meth)acrylates, $C_1$-$C_6$ alkyl (meth)acrylamides and combinations thereof; and (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein the polymer has a glass transistion temperature of greater than about 45° C.

In a second aspect, the invention provides a composition comprising a polymer comprising repeating units derived from (a) from 16% by weight to about 35% by weight of said polymer of at least one N-vinyl lactam monomer; (b) at least one monomer selected from the group consisting of functionalized and unfunctionalized $C_1$-$C_6$ alkyl (meth)acrylates, $C_1$-$C_6$ alkyl (meth)acrylamides and combinations thereof; and (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein the polymer has a glass transistion temperature of greater than about 45° C. Non-limiting examples of such compositions include personal care compositions, coating compositions, Household, Industrial and Institutional compositions, pharmaceutical compositions, food compositions, cementing fluids, oilfield compositions, construction compositions, servicing fluids, gravel packing muds, fracturing fluids, completion fluids, workover fluids, spacer fluids, drilling muds, biocides, adhesives, inks, papers, polishes, membranes, metal working fluids, plastics, textiles, printing compositions, lubricants, preservatives, agrochemicals, and wood-care compositions. Particularly, the composition is a personal care composition.

In a third aspect, the invention provides a method for protecting a keratinous substrate from UV radiation comprising applying onto the substrate a composition comprising: (a) a polymer comprising repeating units derived from: from 16% by weight to about 35% by weight of said polymer of at least one N-vinyl lactam monomer; at least one monomer selected from the group consisting of functionalized and unfunctionalized $C_1$-$C_6$ alkyl (meth)acrylates, $C_1$-$C_6$ alkyl (meth)acrylamides and combinations thereof; and at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof, wherein the polymer has a glass transistion temperature of greater than about 45° C.; and (b) at least one UV active.

DESCRIPTION OF THE DRAWINGS

Each of FIGS. 1 to 4 depict the percent water resistance study of sun care formulations comprising polymers according to the invention in comparison to various commercially available formulations.

DETAILED DESCRIPTION

Figure 1:
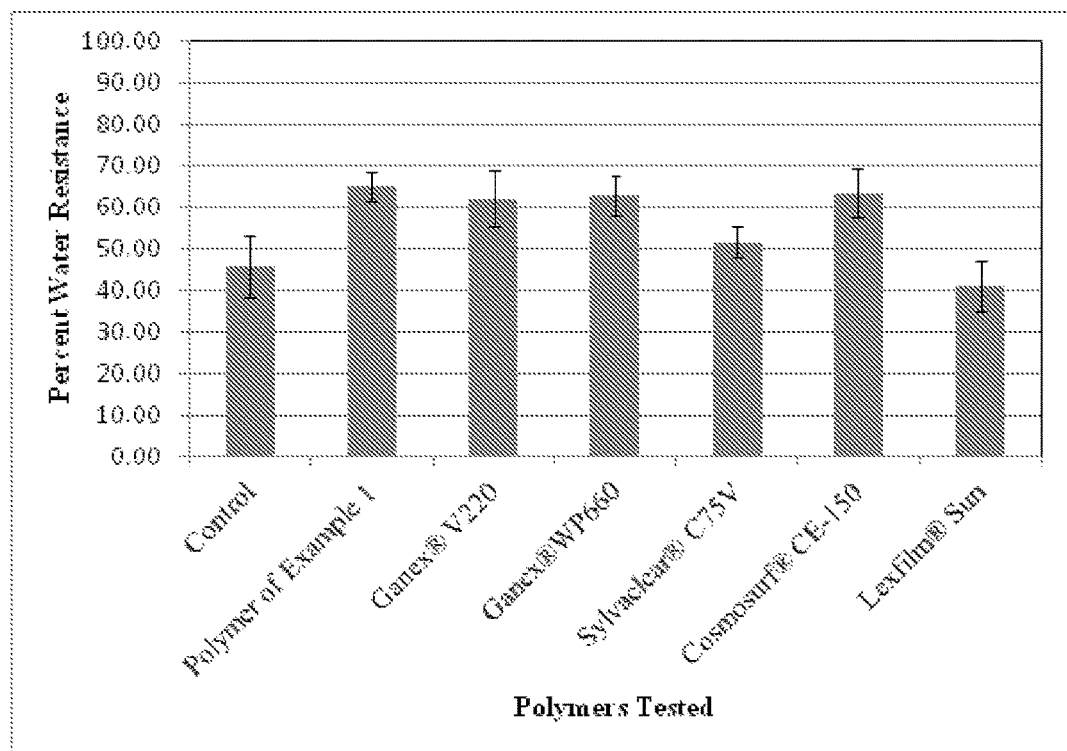

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description or illustrated in the drawings. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the disclosed and/or claimed inventive concept(s) have been described in terms of particular aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAAB-CCCC, CBBAAA, CABABB, and so forth. The skilled artisan will understand that typically there is no limit on the number of items or terms in any combination, unless otherwise apparent from the context.

The term "each independently selected from the group consisting of" means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized monovalent straight-chain or branched-chain $C_1$-$C_{60}$ group optionally having one or more heteroatoms. Particularly, an alkyl is a $C_1$-$C_{45}$ group and more particularly, a $C_1$-$C_{30}$ group. Non-limiting examples of alkyl groups include methyl, ethyl, n-propyl, isopropyl, n-butyl, isobutyl, tert-butyl, n-pentyl, isopentyl, n-hexyl, n-heptyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "alkylene" refers to a functionalized or unfunctionalized divalent straight-chain or branched-chain $C_1$-$C_{40}$ group optionally having one or more heteroatoms. Particularly, an alkylene is a $C_1$-$C_{30}$ group and more particularly, a $C_1$-$C_{20}$ group. Non-limiting examples of alkylene groups include —$CH_2$—. —$CH_2$—$CH_2$—, —$CH(CH_3)$—$CH_2$—, —$CH_2$—$CH(CH_3)$—, —$C(CH_3)_2$—, —$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, and —$CH_2$—$CH_2$—$CH_2$—$CH_2$—$CH_2$—$CH_2$—$CH_2$—.

The term "heteroatom" refers to oxygen, nitrogen, sulfur, silicon, phosphorous, and/or halogen. The heteroatom(s) may be present as a part of one or more heteroatom-containing functional groups. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups.

The term "halogen" refers to chloro, bromo, iodo and/or fluoro.

The term "ammonium" includes protonated $NH_3$ and protonated primary, secondary, and tertiary organic amines.

The term "functionalized" refers to the state of a moiety that has one or more functional groups introduced to it by way of one or more functionalization reactions known to a person having ordinary skill in the art. Non-limiting examples of functionalization reactions include epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like.

The term "residue of" refers to a fragment of a reactant that remains after a reaction with another reactant(s). The residue may be mono-, di- or polyvalent.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. The term includes both branched and hyper-branched structures.

The term "free radical addition polymerization initiator" refers to a compound used in a catalytic amount to initiate a free radical addition polymerization. The choice of initiator depends mainly upon its solubility and its decomposition temperature.

The term "alkyl (meth) acrylate" refers to an alkyl ester of acrylic and/or methacrylic acid.

The term "alkyl (meth) acrylamide" refers to an alkyl amide of acrylic and/or methacrylic acid.

The "glass transition temperature" (Tg) of a polymer is characterized by a change from a relatively hard, brittle, glassy material to a soft, more flexible, flowable material as the temperature is raised through the glass transition temperature.

The terms "personal care composition" and "cosmetics" refer to compositions intended for use on or in the human body, such as skin, sun, hair, oral, cosmetic, and preservative compositions, including those to alter the color and appearance of the skin and hair.

The term "sun care composition" refers to any composition intended for use on the human body for protection from harmful or undesirable radiation from the sun.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "pharmaceutically active ingredient" should be construed in a broad sense as including any ingredient considered to have a therapeutic effect when delivered to a subject in need thereof and further being regulated by drug authorities like CDER, EMEA, TAG etc. Pharmaceutically active ingredients may act systemically upon oral consumption, or locally such as when present in the buccal cavity, on the skin, etc. They may also be delivered across the skin as in transdermal drug delivery systems.

The term "oilfield composition" refers to a composition that may be used in the exploration, extraction, recovery, and/or completion of any hydrocarbon. Non-limiting examples of oilfield compositions include cement fluids, anti-agglomerants, kinetic hydrate inhibitors, shale swelling inhibitors, drilling fluids, drilling muds, servicing fluids, gravel packing muds, friction reducers, fracturing fluids, completion fluids, and work over fluids.

The term "servicing fluid" refers to a fluid used to drill, complete, work over, fracture, or in any way prepare a well bore for the recovery of materials residing in a subterranean formation penetrated by the well bore. It is understood that "subterranean formation" encompasses both areas below exposed earth or areas below earth covered by water such as sea or ocean water. Examples of servicing fluids include, but are not limited to, a drilling fluid or mud, a cement slurry, a gravel packing fluid, a fracturing fluid, a completion fluid, and a workover fluid, all of which are well known in the art.

The term "performance chemicals composition" refers to any non-personal care composition. Performance chemicals compositions serve a broad spectrum of arts, and include non-limiting compositions such as: adhesives, agricultural, biocides, coatings, electronics, household-industrial-institutional (HI&I), inks, membranes, metal fluids, oilfield, paper, paints, plastics, printing, construction, and wood-care compositions.

The term "coating composition" refers to any composition suitable for application on a substrate in order to provide one or more desired functions, including, but not limited to protecting, smoothing, strengthening, decorating, color enhancing/altering, substrate preparing and/or texturizing. The substrate for a coating composition may include, without limitation, paper, paper board, wood, inorganic substrate, woven and non-woven textiles, metal, leather, powder, plastic, polymer, glass, cement, ceramic, traffic, tile, rubber, sealant, cable, concrete, plasterboard, adhesives, fillers, primers, inks, fertilizers, pharmaceuticals, structural materials, molding, printing, inks, and the like. Examples of coating compositions include, without limitation, the following: paints, primers, stains, sealers, varnishes/polyurethanes, adhesives, waterproofers, wood hardeners. Coating compositions may be applied by brush, dauber, roll, strip/sheet, and/or trowel, or may be atomized and applied as a spray, mist, or droplet.

A "paint composition" is a non-limiting, specific type of a "coating composition". Paints may be water based or non-water based (i.e., solvent based). Paint compositions may be designed for any number of substrates, including wood, siding, dry wall, plaster, plastics, masonry, brick, tile, particle board, glass, stucco, concrete, and the like. Non-limiting examples of paints include exterior paints, interior paints, architectural paints, and automotive paints.

All percentages, ratio, and proportions used herein are based on a weight basis unless other specified.

In a first aspect, the invention provides a polymer comprising repeating units derived from (a) from 16% by weight to about 35% by weight of said polymer of at least one N-vinyl lactam monomer; (b) at least one monomer selected from the group consisting of functionalized and unfunctionalized $C_1$-$C_6$ alkyl (meth)acrylates, $C_1$-$C_6$ alkyl (meth)acrylamides and combinations thereof; and (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein the polymer has a glass transistion temperature of greater than about 45° C.

The N-vinyl lactam has a structure:

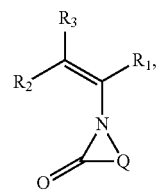

wherein Q is a functionalized or unfunctionalized $C_1$-$C_{10}$ alkylene and each $R_1$, $R_2$, and $R_3$ is independently selected from the group consisting of hydrogen and functionalized and unfunctionalized $C_1$-$C_4$ alkyl groups. Non-limiting examples of Q include functionalized and unfunctionalized —$CH_2$—$CH_2$—, —$CH_2$—$CH_2$—$CH_2$—, —$CH_2$—$CH_2$—$CH_2$—$CH_2$—, and —$CH_2$—$CH_2$—$CH_2$—$CH_2$—$CH_2$— groups. Particularly, Q is —$CH_2$—$CH_2$—$CH_2$— or —$CH_2$—$CH_2$—$CH_2$—$CH_2$—$CH_2$— group. Particularly, each $R_1$, $R_2$, and $R_3$ is independently selected from the group consisting of hydrogen and methyl groups. More particularly, each $R_1$, $R_2$, and $R_3$ is hydrogen.

Non-limiting examples of N-vinyl lactams include N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and combinations thereof. Particularly, N-vinyl lactam is selected from the group consisting of N-vinyl-2-pyrrolidone, N-vinyl-2-piperidone, and N-vinyl-2-caprolactam. More particularly, N-vinyl lactam is N-vinyl-2-pyrrolidone.

Non-limiting examples of $C_1$-$C_6$ alkyl (meth)acrylates include methyl (meth)acrylate, ethyl (meth)acrylate, propyl (meth)acrylate, iso-butyl (meth)acrylate, sec-butyl (meth)acrylate, tert-butyl (meth)acrylate, n-pentyl (meth)acrylate, iso-amyl (meth)acrylate, n-hexyl (meth)acrylate, and combinations thereof. Particularly, $C_1$-$C_6$ alkyl (meth)acrylate is selected from the group consisting of methyl (meth)acrylate, ethyl (meth)acrylate, and combinations thereof. More particularly, $C_1$-$C_6$ alkyl (meth)acrylate is methyl (meth)acrylate.

Non-limiting examples of $C_1$-$C_6$ alkyl (meth)acrylamides include methyl (meth)acrylamide, N,N-dimethyl (meth)acrylamide, ethyl (meth)acrylamide, propyl (meth)acrylamide, iso-butyl (meth)acrylamide, sec-butyl (meth)acrylamide, tert-butyl (meth)acrylamide, n-pentyl (meth)acrylamide, iso-amyl (meth)acrylamide, n-hexyl (meth)acrylamide, and combinations thereof. Particularly, $C_1$-$C_6$ alkyl (meth)acrylamide is selected from the group consisting of methyl (meth)acrylamide, ethyl (meth)acrylamide, N,N-dimethyl (meth)acrylamide and combinations thereof. More particularly, $C_1$-$C_6$ alkyl (meth)acrylamide is methyl (meth)acrylamide.

Non-limiting examples of $C_8$-$C_{30}$ branched alkyl (meth)acrylates include 2-ethylhexyl (meth)acrylate; 1,1,3,3-tetramethylbutyl (meth)acrylate; 1,1-dimethylhexyl (meth)acrylate; 6-methylheptyl (meth)acrylate; 7-methyloctyl (meth)acrylate; 2-propylheptyl (meth)acrylate; 8-methylnonyl (meth)acrylate; 9-methyldecyl (meth)acrylate; 10-methylundecyl (meth)acrylate; 11-methyldodecyl (meth)acrylate; 12-methyltridecyl (meth)acrylate; 13-methyltetradecyl (meth)acrylate; 14-methylpentadecyl (meth)acrylate; 15-methylhexadecyl (meth)acrylate; 16-methylheptadecyl (meth)acrylate; 17-methyloctadecyl (meth)acrylate; and combinations thereof. Particularly, $C_8$-$C_{30}$ branched alkyl (meth)acrylate is selected from the group consisting of 2-ethylhexyl (meth)acrylate; 1,1,3,3-tetramethylbutyl (meth)acrylate and combinations thereof. More particularly, $C_8$-$C_{30}$ branched alkyl (meth)acrylate is 2-ethylhexyl (meth)acrylate.

Non-limiting examples of $C_8$-$C_{30}$ branched alkyl (meth)acrylamides include N-2-ethylhexyl (meth)acrylamide; N-1,1,3,3-tetramethylbutyl (meth)acrylamide; N-1,1-dimethylhexyl (meth)acrylamide; N-6-methylheptyl (meth)acrylamide; N-7-methyloctyl (meth)acrylamide; N-2-propylheptyl (meth)acrylamide; N-8-methylnonyl (meth)acrylamide; N-9-methyldecyl (meth)acrylamide; N-10-methylundecyl (meth)acrylamide; N-11-methyldodecyl (meth)acrylamide; N-12-methyltridecyl (meth)acrylamide; N-13-methyltetradecyl (meth)acrylamide; N-14-methylpentadecyl (meth)acrylamide; N-15-methylhexadecyl (meth)acrylamide; N-16-methylheptadecyl (meth)acrylamide; N-17-methyloctadecyl (meth)acrylamide; and combinations thereof. Particularly, $C_8$-$C_{30}$ branched alkyl (meth)acrylamide is selected from the group consisting of N-2-ethylhexyl (meth)acrylamide; N-1,1,3,3-tetramethylbutyl (meth)acrylamide; and combinations thereof. More particularly, $C_8$-$C_{30}$ branched alkyl (meth)acrylamide is N-2-ethylhexyl (meth)acrylamide.

Particularly, polymers according to the invention comprise repeating units derived from: (a) from 18% by weight to about 25% by weight of said polymer of at least one monomer selected from the group consisting of N-vinyl-2-pyrrolidone, N-vinyl-2-caprolactam, and combinations thereof; (b) at least one monomer selected from the group consisting of methyl (meth)acrylate, methyl (meth)acrylamide, tert-butyl (meth)acrylate, tert-butyl (meth)acrylamide, N,N-dimethyl (meth)acrylamide, and combinations thereof; and (c) at least one monomer selected from the group consisting of 2-ethylhexyl (meth)acrylate; N-2-ethylhexyl (meth)acrylamide; 1,1,3,3-tetramethylbutyl (meth)acrylate; N-1,1,3,3-tetramethylbutyl (meth)acrylamide; and combinations thereof.

More particularly, the polymer comprises repeating units derived from: (a) from 18% by weight to about 25% by weight of said polymer of at least one monomer selected from the group consisting of N-vinyl-2-pyrrolidone, N-vinyl-2-caprolactam, and combinations thereof; (b) from about 25% by weight to about 50% by weight of said polymer of at least one monomer selected from the group consisting of methyl (meth)acrylate, methyl (meth)acrylamide, tert-butyl (meth)acrylate, tert-butyl (meth)acrylamide, N,N-dimethyl (meth)acrylamide, and combinations thereof; and (c) from about 30% by weight to about 70% by weight of said polymer of at least one monomer selected from the group consisting of 2-ethylhexyl (meth)acrylate; N-2-ethylhexyl (meth)acrylamide; 1,1,3,3-tetramethylbutyl (meth)acrylate; N-1,1,3,3-tetramethylbutyl (meth)acrylamide; and combinations thereof.

Even more particularly, the polymer comprises repeating units derived from: (a) from 18% by weight to about 25% by weight of said polymer of N-vinyl-2-pyrrolidone, (b) from about 25% by weight to about 50% by weight of said polymer of methyl (meth)acrylate, and (c) from about 30% by weight to about 70% by weight of said polymer of 2-ethylhexyl (meth)acrylate.

Particularly, the polymer according to the invention has a structure selected from the group consisting of:

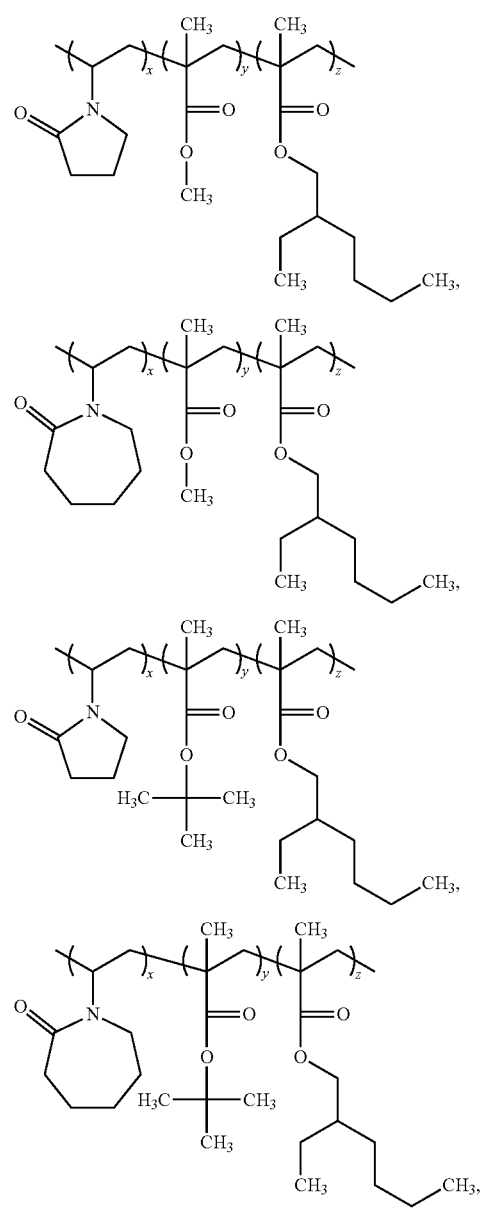

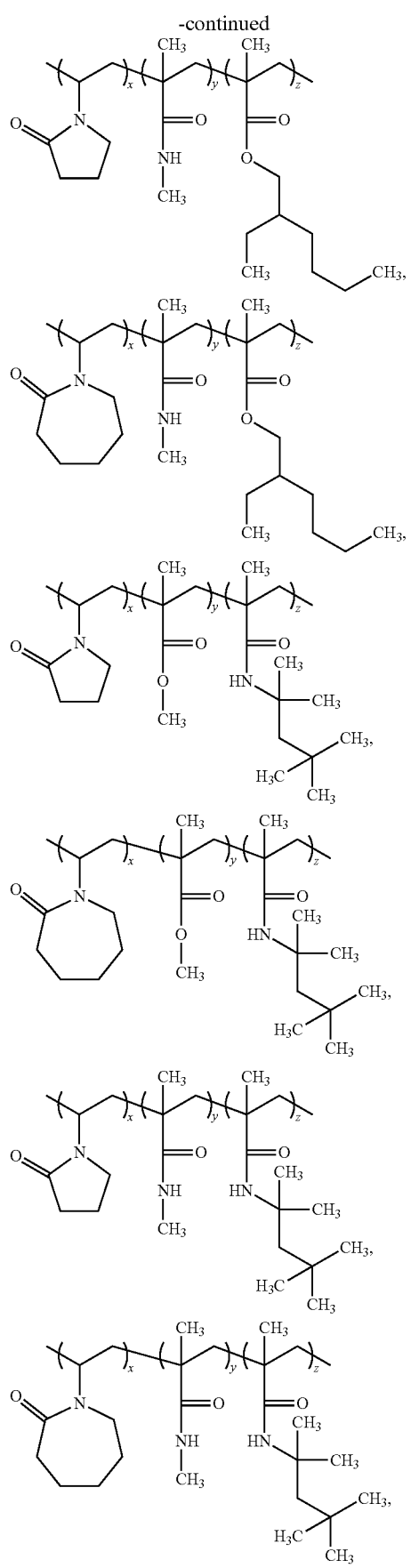
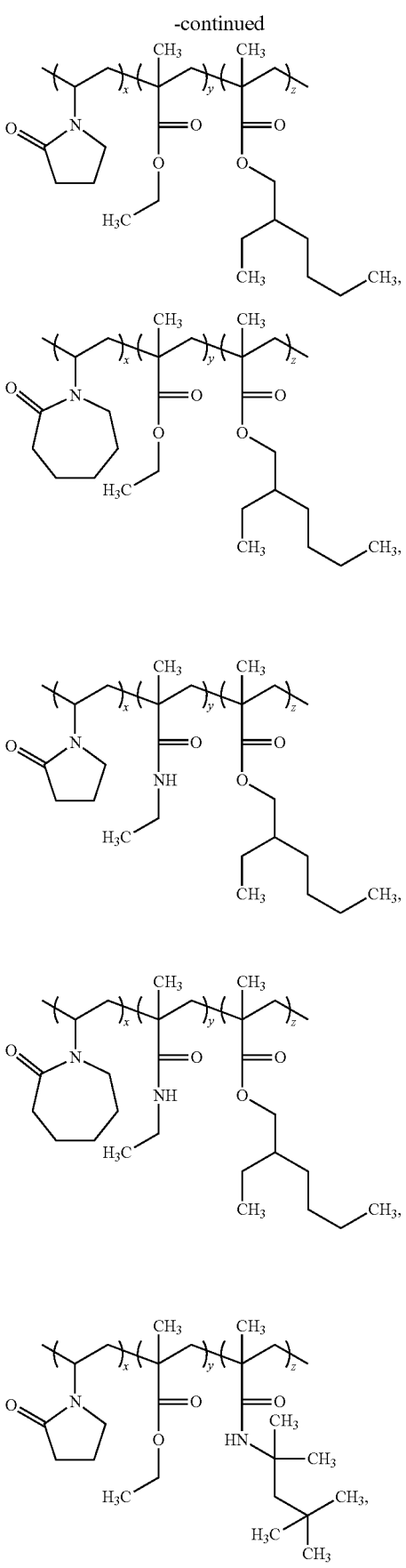

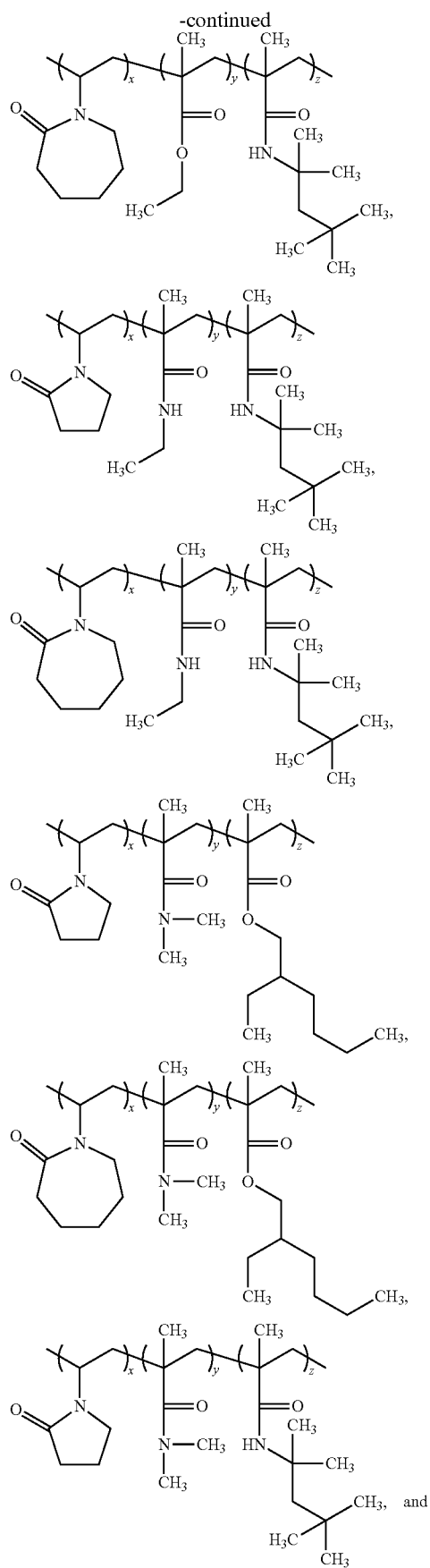
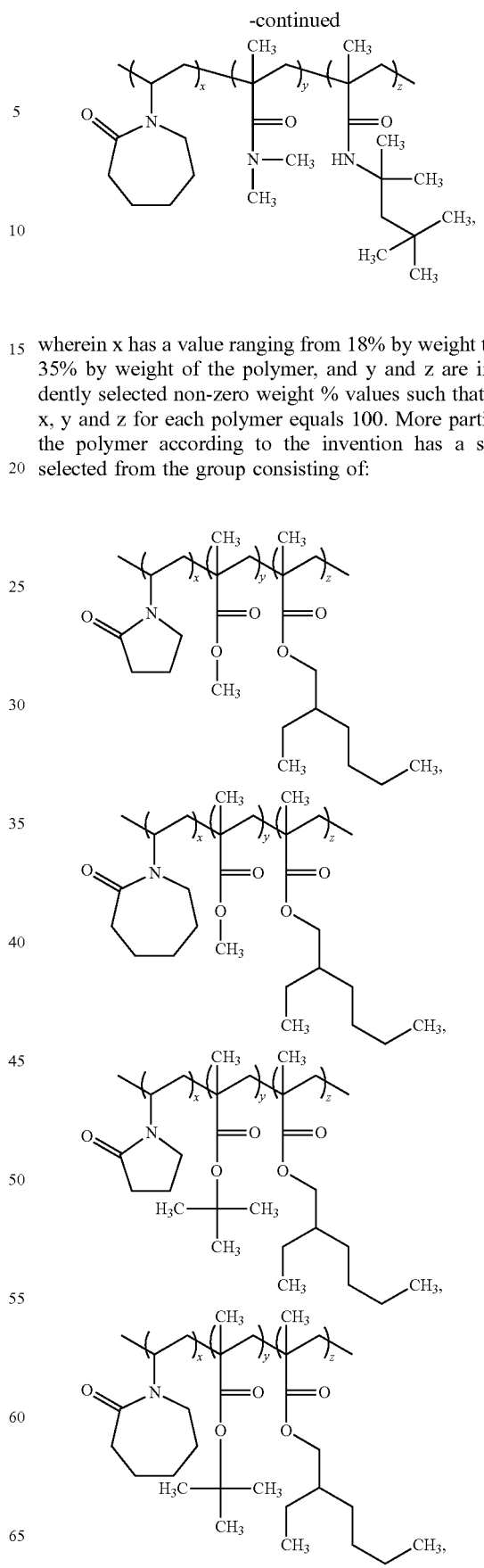
wherein x has a value ranging from 18% by weight to about 35% by weight of the polymer, and y and z are independently selected non-zero weight % values such that sum of x, y and z for each polymer equals 100. More particularly, the polymer according to the invention has a structure selected from the group consisting of:

-continued

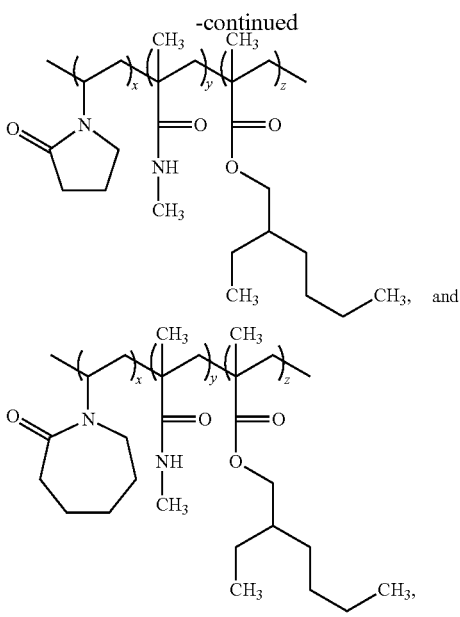

wherein x has a value ranging from 18% by weight to about 35% by weight of the polymer, and y and z are independently selected non-zero weight % values such that sum of x, y and z for each polymer equals 100. Even more particularly, the polymer has a structure:

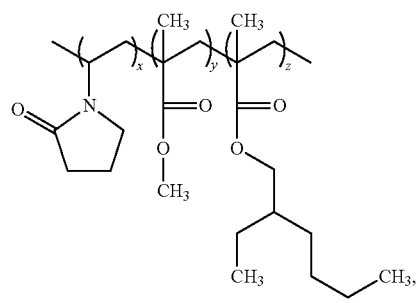

wherein x has a value ranging from 18% by weight to about 35% by weight of the polymer, and y and z are independently selected non-zero weight % values such that sum of x, y and z for each polymer equals 100.

Particularly, x has a value ranging from 18% by weight to about 35% by weight of the polymer; more particularly, from 18% by weight to about 30% by weight of the polymer; and even more particularly, from 18% by weight to about 25% by weight of the polymer.

Particularly, y has a value ranging from about 15% by weight to about 75% by weight of the polymer; more particularly, from about 20% by weight to about 60% by weight of the polymer; and even more particularly, from about 25% by weight to about 50% by weight of the polymer.

Particularly, z has a value ranging from about 20% by weight to about 90% by weight of the polymer; more particularly, from about 25% by weight to about 80% by weight of the polymer; and even more particularly, from about 30% by weight to about 70% by weight of the polymer.

The weight % values of constituent monomers for each polymer disclosed herein are such that their sum for each polymer equals 100.

The polymers according to the invention have a glass transition temperature ranging from about 45° C. to about 85° C. More particularly, the glass transition temperature ranges from about 50° C. to about 75° C. Even more particularly, the glass transition temperature ranges from about 55° C. to about 70° C.

The polymers according to the invention may be used alone or in combination with other ingredient(s) in various compositions and product forms.

In a second aspect, the invention provides a composition comprising a polymer comprising repeating units derived from (a) from 16% by weight to about 35% by weight of said polymer of at least one N-vinyl lactam monomer; (b) at least one monomer selected from the group consisting of functionalized and unfunctionalized $C_1$-$C_6$ alkyl (meth)acrylates, $C_1$-$C_6$ alkyl (meth)acrylamides and combinations thereof; and (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein the polymer has a glass transistion temperature of greater than about 45° C.

Non-limiting examples of compositions include personal care compositions, coating compositions, pharmaceutical compositions, coating compositions, household, industrial and institutional compositions, cementing fluids, oilfield compositions, construction compositions, servicing fluids, gravel packing muds, fracturing fluids, completion fluids, workover fluids, spacer fluids, drilling muds, food compositions, biocides, adhesives, inks, papers, polishes, membranes, metal working fluids, plastics, textiles, printing compositions, lubricants, preservatives, agricultural compositions, and wood-care compositions. Particularly, the composition is a personal care composition, coating composition, household, industrial and institutional composition, pharmaceutical composition, or an agricultural composition. More particularly, the composition is a personal care composition.

Non-limiting examples of personal care compositions that may comprise polymer(s) according to the invention include sun care compositions, face care compositions, lip care compositions, eye care compositions, skin care compositions, after-sun compositions, body care compositions, nail care compositions, anti-aging compositions, insect repellants, oral care compositions, deodorant compostions, hair care compositions, conditioning compositions, color cosmetic compositions, color-protection compostions, self-tanning compositions, and foot care compositions.

Particularly, the personal care composition is a sun care composition. More particularly, the personal care composition is a water-resistant sun care composition.

Typically, sun care compositions may also comprise one or more UV actives. Non-limiting examples of UV actives include organic and inorganic materials that scatter, absorb, and/or reflect radiation having a wavelength from about 100 nm to about 400 nm.

In one particular aspect, the sun care composition protects against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another aspect, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV actives (or UV filters) that may be included in the personal care compositions most likely will depend on local regulations. As the rules governing the names and usage levels evolve over time, it is impossible to include every UV absorber that may be used with the invention.

Non-limiting examples of suitable UV actives include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; 2-(1,1-dimethylethyl)-6-[[3-(1,1-dimethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; n-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylenediamine; benzophenone-8; ethyl-4-bis(hydroxypropyl) aminobenzoate; 6-tert-butyl-2-(5-chloro-2H-benzotriazole-2-yl)-4-methylphenol; p-aminobenzoic acid; 3,3',3",5,5',5"-hexa-tert-butyl-α-α'-α"-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxylmethyl}-propane; ethylhexyl p-methoxycinnamate, and blends thereof.

Particularly, the UV filters that may be used in the water-resistant sun care compositions comprising the polymers according to the invention include one or more of: Bemotrizinol (Escalol™ S UV filter (Ashland)), Padimate O (Escalol™ 507 UV filter (Ashland)), Avobenzone (Escalol™ 517 UV filter (Ashland)), Octinoxate (Escalol™ 557 UV filter (Ashland)), Oxybenzone (Escalol™ 567 UV filter (Ashland)), Sulisobenzone (Escalol™ 577 UV filter (Ashland)), Octisalate (Escalol™ 587 UV filter (Ashland)), Homosalate (Escalol™ HMS UV filter (Ashland)), and Octocrylene (Escalol™ 597 UV filter (Ashland)).

The water-resistant sun care compositions according to the invention may further comprise at least one additive selected from the group consisting of secondary polymers for improving water-resistance, UV active solubilizers, oils, waxes, solvents, emulsifiers, preservatives, antioxidants, vitamins, perfumes, insect repellants, dyes, pigments, humectants, fillers, thickeners, film formers, stabilizers, buffers, spreading agents, pearlizing agents, electrolytes, acids, bases, pharmaceutically or dermatologically or cosmetically acceptable excipients, and combinations thereof.

Non-limiting, yet particular examples of water-resistant sun care compositions according to the invention include an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous gel, an aqueous gel, an alcoholic solution or a hydro-alcoholic solution.

In particular aspects, the polymer according to the invention is present in an amount from about 0.01% by weight to about 20% by weight of the sun care compositions described herein. More particularly, the polymer is present from about 0.1% by weight to about 10% by weight of the sun care composition. Even more particularly, the polymer is present from about 0.25% by weight to about 5.0% by weight of the sun care composition.

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Non-limiting applications of hair care compositions include: hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and protecting hair from UV radiation.

The hair care compositions may further comprise one or more additional ingredients. Particularly, the additional ingredients may be selected from the group consisting of: skin care or hair care agents, hair styling agents, hair fixative agents, film formers, structurants, gelling agents, surfactants, thickeners, preservatives, viscosity modifiers, electrolytes, pH adjusting agents, perfumes, dyes, organosilicon compounds, anti-dandruff agents, anti-foaming agents, anti-frizz agents, penetrants, vitamins, conditioning agents, chelating agents, antimicrobial agents, preservatives, UV absorbers, sunscreens, natural extracts, propellants, carriers, diluents, solvents, pharmaceutical actives, lubricants, combing aids, plasticizers, solubilizers, neutralizing agents, vapor pressure suppressants, bleaching agents, hydrating agents, moisturizers, cosmetic adjuvants and/or additives, protectants, and mixtures thereof.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by Ashland Specialty Ingredients: *Health and nutrition product guide—Performance enhancing products* (08/2008), *Plasdone™ povidones product overview* (04/2010), *Plasdone™ K-12 and K-17 povidones—Solubilizers for liquid softgel fill compositions* (09/2010), *Plasdone™ K-29/32 povidone—High efficiency binder for wet granulation* (04/2010), *Plasdone™ S-630 copovidone—Product Overview* (04/2010), *Polyplasdone™ Ultra and Ultra-10 crospovidones—Product overview* (09/2010), *Polyplasdone™ superdisintegrants—Product overview* (07/2010), *Polyplasdone™ crospovidone—Superdisintegrants for orally disintegrating and chewable tablets* (07/2010), *Polyplasdone™ crospovidone—Nonionic superdisintegrant for improved dissolution of cationic drugs* (07/2009), *Polyplasdone™ crospovidone—The solution for poorly soluble drugs* (07/2009), *Polyplasdone™ crospovidone—Novel pelletization aid for extrusion spheronization* (07/2010), *PVP-Iodine povidone iodine antiseptic agent* (03/2004), and *Pharmaceutical technical bulletin—PVP-Iodine for prophylaxis and treatment of bovine mastitis* (12/2003). Each publication is hereby incorporated in its entirety by reference.

Any range in composition pH may be used. In aspects wherein the composition may be applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, α-hydroxyacids, β-hydroxyacids, α,β-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

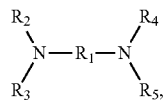

wherein $R_1$ may be a propylene residue that may be optionally substituted with an hydroxyl group or a $C_1$-$C_4$ alkyl radical; $R_2$, $R_3$, $R_4$ and $R_5$ are identical or different and represent a hydrogen atom, a $C_1$-$C_4$ alkyl radical or $C_1$-$C_4$ hydroxyalkyl radical.

The composition may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by Ashland Specialty Ingredients, each of which is hereby incorporated in its entirety by reference: *Plasdone™ K-29/32, Advanced non-oxidative, non-abrasive teeth whitening in toothpastes, mouthwashes, and oral rinses* (2010), *Polymers for oral care, product and applications guide* (2002), *A composition guide for excellent hair styling gels and lotions* (4/2003), *PVP (polyvinylpyrrolidone)* (no date provided), and *Textile chemicals, solutions for the most challenging product environment* (no date provided).

Also contemplated are additional personal care compositions that may comprise the polymers described herein. Disclosures on such compositions may be found in the publications listed below, each of which is hereby incorporated in its entirety by reference: (1) Prototype Compositions—Personal Care Products (2009) from Xiameter, Dow Corning. (2) Sun care compositions under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorohydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin tighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference.

Non-limiting examples of structurants that may be used in the hair care compositions according to the invention include dextrin palmitate, trihydroxystearin, hydroxy stearic acid, hydrophilic or hydrophobic silica, hydrophobically modified clay selected from the group consisting of stearalkonium hectorite, quaternium-18 bentonite, quaternium-18 hectorite, disteardimonium hectorite, derivatives thereof, and mixtures thereof.

The hair care compositions of the invention may additionally comprise one or more hair styling agents, hair fixative agents, and/or film formers.

Particularly useful as styling agents are hair styling polymers. The hair styling polymers may be cationic, anionic, amphoteric or nonionic in nature. The polymers may be synthetic or naturally derived. Non-limiting examples of hair styling polymers include the following polymer products available for sale from Ashland Specialty Ingredients: (1) Cationic styling polymers with hair conditioning benefits—Styleze™ W Polymer, Styleze™ CC-10 (pseudo cationic), Gafquat™ 755 NP, and Gafquat™ 440; (2) Styling polymers with excellent high humidity curl retention—Styleze™ 2000, Allianz™ LT 120, Styleze™ W Polymer, and Advantage™ LCA; (3) Non-ionic styling polymers with broad ingredient compatibility—Polyvinylpyrrolidones such as PVP K-30, PVP K-60 and PVP K-90, Vinylpyrrolidone/vinyl acetate copolymers such as PVP/VA (E, I or W) 735, PVP/VA (E or W) 635, PVP/VA (E or I) 535, PVP/VA (E or I) 335 and PVP/VA S-630, and poly(vinylpyrrolidone/dimethylaminoethylmethacrylate) polymers such as Copolymer 845/937. Additional details on the aforementioned polymers and methods of use, or compositions thereof, may be found in a publication from Ashland Specialty Ingredients titled "*A Composition Guide for Excellent Hair Styling Gels and Lotions*" (2002) that is hereby incorporated in its entirety by reference.

A non-limiting example of hair fixative agent that may be used in hair care compositions according to the invention includes a hair fixative polymer available for sale from Ashland Specialty Ingredients, AquaStyle™ 300 (INCI name Polyquaternium-69). A related publication from Ashland Specialty Ingredients titled "*Aquastyle® 300, A Fixative Polymer with Enhanced Styling Benefits*" (2007) is hereby incorporated in its entirety by reference.

Non-limiting examples of film formers that may be used in hair care compositions according to the invention include film forming polymers available for sale from Ashland Specialty Ingredients such as (1) Aquaflex™ FX 64, (2) AquaCat™ clear cationic solution, (3) Aqualon™ carboxymethylcellulose, (4) Klucel™ hydroxypropylcellulose, and (5) Primaflo™ HP22 polymer solution.

Further details on hair styling agents, hair fixative agents, and/or film formers may be found in U.S. Pat. Nos. 7,871,600, 7,205,271, 7,122,175, 7,041,281, 6,998,114, 6,749,836, 6,689,346, 6,599,999, 6,562,325, 6,413,505, 6,387,351, 6,228,352, 5,643,581, 5,922,312, 5,897,870, 5,879,669, 5,709,850, 5,753,216 and 5,632,977 each of which is hereby incorporated in its entirety by reference.

Non-limiting examples of anti-frizz agents that may be used in hair care compositions according to the invention include anti-frizz polymers available for sale from Ashland Specialty Ingredients such as AquaStyle™ 300 and Styleze™ XT3. Information on related anti-frizz agents may be found in U.S. Pat. Nos. 7,914,773, 7,785,575, and U.S. published application 2010/00093584, the disclosures of each of which is hereby incorporated in its entirety by reference.

One or more plasticizers or coalescing agents may be added to modify the film forming characteristics of hair care compositions according to the invention. Non-limiting examples of plasticizers include glycols, adipic esters, phthalate esters, isobutyrate esters, terephthalate esters, epoxidized butyl esters or fatty acids, epoxidized vegetable oils, glycerine, di-2-ethylhexyladipate or dioctyladipate (DOA), di-2-ethylhexyl phthalate or dioctyl phthalate (DOP), di-2-ethylhexyl terephthalate (DOTP), dicyclohexyl phthalate, diisononyl adipate, diisononylphthalate, n-butyl benzyl phthalate, 1,3-butylene glycol/adipic acid polyester, dialkyl adipate, dialkyl phthalate derivatives where the alkyl group is a $C_1$-$C_{12}$ alkyl group, di-n-hexylazelate, diphenylphthalate, tricresol phosphate, benzyl benzoate, dibutyl phosphate, tributyl phosphate, tributoxyethyl phosphate, triphenyl phosphate, butyl acetyl ricinoleate, glycerol acetyl ricinoleate, dibutyl phthalate, diethyl phthalate, dioctyl phthalate, dimethoxyethyl phthalate, diisobutyl phthalate, diamyl phthalate, dibutyl glycolate, butyl stearate, triethyl citrate, tributyl citrate, tributyl acetyl citrate, 2-hexyltriethylacetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3-pentanediol diisobutyrate (TXIB), methyl abietate, cumyl acetate, dibutoxyethyl adipate, di-n-hexylazelate, glyceryl-tri-benzerate, tri-n-butylcitrate, dioctyl fumarate, triisonyl trimellitate, dioctyl isophthalate, butyl oleate, chlorinated paraffin, tricresolphosphate, dibutyl sebacate, dimethicone copolyol (Dow Corning 190), PEG-6 capric/caprylic glyceride (SOFTIGEN 767), DIACETIN, LAURAMIDE DEA (MONAMID 716), phenyl trimethicone (ABIL AV 20-1000), propylene glycol, dipropylene glycol, as well as polymeric plasticizers, and mixtures thereof. Non-limiting examples of coalescing solvents include acetone, methyl acetate, and di- or tri-propylene glycol methyl ethers, and mixtures thereof. Further examples of plasticizers may be found in U.S. Pat. Nos. 5,753,216 and 5,676,935, the disclosures of each of which are hereby incorporated in its entirety by reference.

Non-limiting examples of propellants that may be used in hair care compositions of the invention include trichlorofluoromethane, chlorodifluoromethane, 1,1-difluoroethane, dichlorotetrafluoroethane, monochlorodifluoromethane, trichlorotrifluoroethane, dimethyl ether, $C_1$-$C_4$ hydrocarbons such as methane, ethane, propane, n-butane, and isobutane, water-soluble gases such as, dimethyl ether, carbon dioxide, and/or nitrous oxide, and insoluble, compressed gases such as nitrogen, helium, and fully-fluorinated oxetanes and oxepanes, and mixtures thereof.

Non-limiting examples of penetrants that may be used in hair care compositions of the invention include lanolin compounds, protein hydrolysates, protein derivatives, and mixtures thereof.

Non-limiting examples of anti-foaming agents that may be used in hair care compositions of the invention include carrier oils, silicone oils, silicone foam inhibitors, hydrophobic silica, hydrophobic fat derivatives, waxes, water-insoluble polymers, amphiphilic components, emulsifiers, coupling agents, and mixtures thereof.

Any known conditioning agent may be used in the personal care compositions of the invention. An extensive discussion on conditioning agents may be found in the book *Conditioning Agents for Skin and Hair, Cosmetic Science and Technology Series*, Volume 21, 1999, Marcel Dekker Publishers. The contents of the book are hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of *eucalyptus*, lavender, vetiver, *litsea cubeba*, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or microemulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaflix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, n-stearoyl phytosphingosine, 2-N-palmitoyl amino-hexadecane-1,3-diol, bis-(N-hydroxy ethyl n-cetyl) malonamide, n-(2-hydroxy ethyl)-N-(3-cetoxyl-2-hydroxy propyl) amide of cetylic acid, n-docosanoyl n-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imidazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), n-Hance™ SP-100 (INCI Name: acrylamidopropyl trimonium chloride/acrylamide copolymer), and n-Hance™ cationic guar (INCI Name: guar hydroxypropyltrimonium chloride) from Ashland Specialty Ingredients (2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze™ 7 and Conditioneze™ NT-20 from Ashland Specialty Ingredients (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bisbiquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, n-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular aspects, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular aspects, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for personal care from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus* gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *caesalpinia spinosa* gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus *aurantium dulcis* (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; *macrocystis pyrifera* (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseed amide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquarternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamine; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; *sclerotium* gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; *sterculia urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, n-Hance™ cationic guar, n-Hance™ HP Series hydroxypropyl guar, n-Hance™ SP-100 conditioning polymer, and Supercol™ guar gum from Ashland Specialty Ingredients (2) Carbopol Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice compositions are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxies, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. No. 3,538,230, and U.S. Pat. No. 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly (methacrylate), poly(ethacrylate), poly(hydroxyalkylmethacrylate), poly(vinyl alcohol), poly(maleic anhydride), poly (maleate) poly(amide), poly(ethylene amine), poly(ethylene glycol), poly(propylene glycol), poly(vinyl acetate), poly (vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in *Kirk-Othmer Encyclopedia of Chemical Technology*, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by $(C_3H_6O_6)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as *thaumatoccous danielli* (Thaumatin I and II) may be used.

The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include *capsicum* and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethyl-idene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly[vinyl methyl ether maleate], or "Gantrez" and its salts). Polyvinylpyrrolidone (povidone) may also be used.

Other components of denture adhesive products impart particular physical attributes to the compositions. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

It is also contemplated that the composition ingredients may be formulated in a single container, or the ingredients may be formulated in-part in two or more distinct containers of the same or different type, the contents of which may require mixing prior to use.

In a third aspect, the invention provides a method for protecting a keratinous substrate from UV radiation comprising applying onto the substrate a water-resistant sun care composition comprising: (a) a polymer comprising repeating units derived from: from 16% by weight to about 35% by weight of said polymer of at least one N-vinyl lactam monomer; at least one monomer selected from the group consisting of functionalized and unfuctionalized $C_1$-$C_6$ alkyl (meth)acrylates, $C_1$-$C_6$ alkyl (meth)acrylamides and combinations thereof; and at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof, wherein the polymer has a glass transistion temperature of greater than about 45° C.; and (b) at least one UV active.

Methods of Synthesis

The polymers according to the invention may be readily synthesized by procedures known by those skilled in the art, non-limiting examples of which include free radical solution polymerization, dispersion polymerization, emulsion polymerization, ionic chain polymerization, living polymerization, and precipitation polymerization.

Free radical polymerization may be used, especially when using water-dispersible and/or water-soluble reaction solvent(s). This type of polymerization method is described in "Decomposition Rate of Organic Free Radical Polymerization" by K. W. Dixon (section II in Polymer Handbook, volume 1, 4th edition, Wiley-Interscience, 1999), which is herein incorporated in its entirety by reference.

Compounds capable of initiating the free-radical polymerization include those materials known to function in the prescribed manner, and include the peroxo and azo classes of materials. Peroxo and azo compounds include, but are not limited to: acetyl peroxide; azo bis-(2-amidinopropane) dihydrochloride; azo bis-isobutyronitrile; 2,2'-azo bis-(2-methylbutyronitrile); benzoyl peroxide; di-tert-amyl peroxide; di-tert-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide;

dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide. Also suitable to initiate the free-radical polymerization are initiator mixtures or redox initiator systems, including: ascorbic acid/iron (II) sulfate/sodium peroxodisulfate, tert-butyl hydroperoxide/sodium disulfite, and tert-butyl hydroperoxide/sodium hydroxymethanesulfinate.

The polymerization reactions may be carried out in the presence of one or more solvents. Non-limiting examples of solvents that may be employed include ethanol, isopropanol, tert-butanol, n-hexane, and Ceraphyl® 230. The polymers may be synthesized in a solvent or a blend of one or more solvents and maintained therein, or the synthesis solvent(s) separated from the polymer by methods known in the art and replaced by a solvent beneficial for formulary development and/or end-use. The polymerization temperature may vary from about 5° C. to about 200° C. The polymerization reaction may be carried out at ambient pressure, sub-atmospheric pressure, or super-atmospheric pressure. The polymerization reaction may be carried out in a batch, continuous and/or semi-continuous manner.

The polymers according to the invention may have a weight-average molecular weight ranging from about 10,000 Da to about 1,000,000 Da, more particularly from about 25,000 Da to about 500,000 Da, and even more particularly from about 50,000 Da to about 250,000 Da.

The molecular weight may be controlled using methods known in the art, including strategies to control the reaction temperature and time, as well as the use of chain-transfer agents such as thiols (e.g., dodecyl mercaptan), and halocarbons (e.g., chlorinated compounds like carbon tetrachloride).

Characterization of Polymers

The polymers and compositions comprising the polymers according to the invention may be analyzed by known techniques. Especially preferred are the techniques of $^{13}$C nuclear magnetic resonance (NMR) spectroscopy, gas chromatography (GC), and gel permeation chromatography (GPC) in order to decipher polymer identity, residual monomer concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses includes the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N. C., *Molar Mass Measurements in Polymer Science*, Halsted Press, 1979; and Billmeyer, F., *Textbook of Polymer Science*, Wiley Interscience, 1984.

The polymers according to the invention may be prepared according to the examples set out below. The examples are presented for purposes of demonstrating, but not limiting, the preparation of the polymers. Therein, the following abbreviations are used:

UV: Ultra violet

VP: N-vinyl-2-pyrrolidone

HPVP: High Purity Vinyl Pyrrolidone

VCap: N-vinyl-2-caprolactam

EHMA: 2-ethylhexyl (meth)acrylate

MMA: Methyl (meth)acrylate

TBA: tert-butyl acrylate

EXAMPLES

Example 1

Synthesis of Poly(VP-Co-MMA-Co-EHMA) with VP/MMA/EHMA Weight Ratio of 20:30:50. Four Hour Feed Reaction in Tert-Butanol Solvent

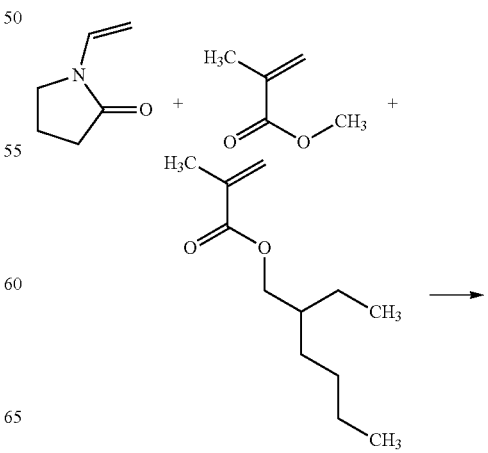

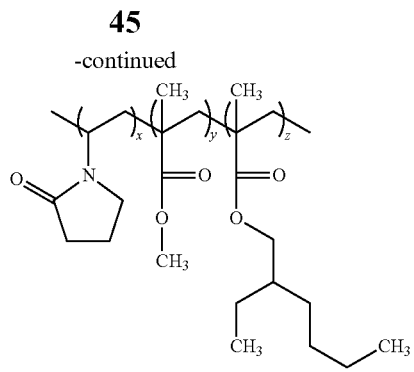

An amount of 36 g of HPVP and 75 g tert-butanol was added to the reaction vessel as a heel charge. The reaction mixture was purged three times with nitrogen while stirring and then heated to 75° C. to 85° C. A pre-mixed feed charge comprising 90 g of EHMA, 54 g of MMA, and tert-butanol was fed in the pump. The feed was started at 70° C. to 80° C. and continued for four hours. The jacket temperature was adjusted to maintain the internal temperature between 80 to 85° C. during the feed. A total amount of 0.9 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 80° C. to 85° C. An amount of 2.0% by weight of total amount of monomers of chaser initiator Luperox® 11 was charged in 12 portions and the reaction sampled for analysis by HPLC. The mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 2

Synthesis of Poly(VP-Co-MMA-Co-EHMA) with VP/MMA/EHMA Weight Ratio of 20:30:50. Two Hour Feed Reaction in Tert-Butanol Solvent

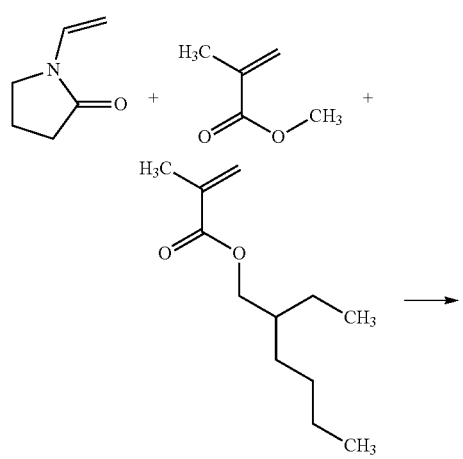

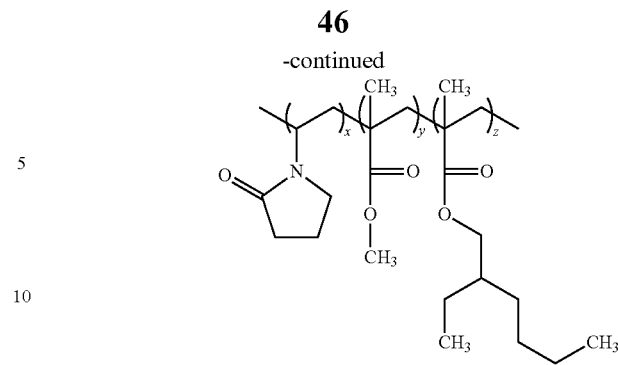

An amount of 36 g of HPVP and 75 g tert-butanol was added to the reaction vessel as a heel charge. The reaction mixture was purged three times with nitrogen while stirring and then heated to 80° C. to 85° C. A pre-mixed feed charge comprising 90 g of EHMA, 54 g of MMA, and 150 g of tert-butanol was fed in the pump. The feed was started at 70° C. to 80° C. and continued for two hours. The jacket temperature was adjusted to maintain the internal temperature between 80 to 85° C. during the feed. A total amount of 0.9 g of the initial initiator Vazo® 67 was charged in two portions during the feed. After the feed was completed, tert-butanol was used to rinse the feeding line, pump and charge line, and discharged into the reaction vessel. The reaction mixture was maintained on hold for one hour at 80° C. to 85° C. An amount of 2.0% by weight of total amount of monomers of chaser initiator Luperox® 121 was charged after every hour after the temperature increased to 90° C. to 91° C. and the reaction sampled for analysis by HPLC. The mixture was maintained on hold for 10 hours at 90° C. to 95° C. The sample was dried under high vacuum at 50° C. to 55° C. In the polymer structure shown, x=20 weight %, y=30 weight % and z=50 weight %.

Example 3

Synthesis of Poly(VP-Co-MMA-Co-EHMA) with VP/MMA/EHMA Weight Ratio of 20:30:50. One Hour Feed Reaction in Tert-Butanol Solvent

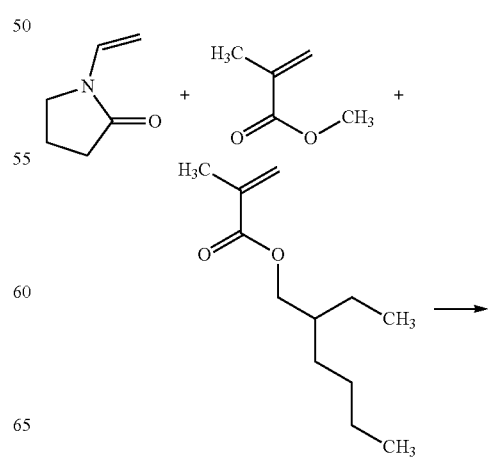

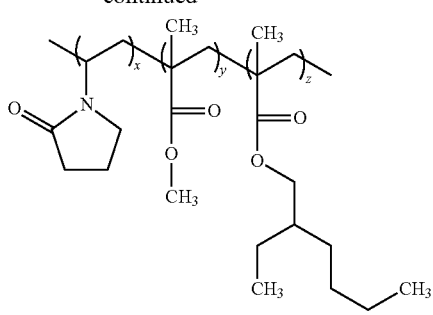

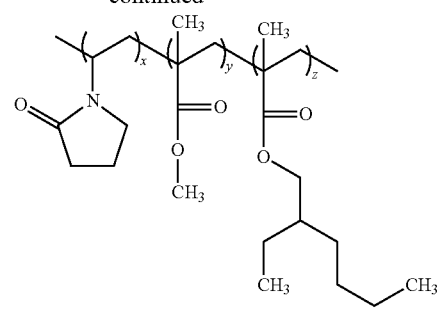

An amount of 36 g of HPVP and 75 g tert-butanol was added to the reaction vessel as a heel charge. The reaction mixture was purged three times with nitrogen while stirring and then heated to 70° C. to 75° C. A pre-mixed feed charge comprising 90 g of EHMA, 54 g of MMA, and tert-butanol was fed in the pump. The feed was started at 70° C. to 75° C. and continued for one hour. The jacket temperature was adjusted to maintain the internal temperature between 70 to 75° C. during the feed. A total amount of 0.9 g of the initial initiator Luperox® 11 was charged in one portion during the feed. After the feed was completed, tert-butanol was used to rinse the feeding line, pump and charge line, and discharged into the reaction vessel. The reaction mixture was maintained on hold for one hour at 85° C. to 90° C. An amount of 2.0% by weight of total amount of monomers of chaser initiator Luperox® 121 was charged in four portions after every hour. The reaction mixture was maintained on hold for 10 hours at 85° C. to 90° C. The sample was dried under high vacuum at 50° C. to 55° C. In the polymer structure shown, x=20 weight %, y=30 weight % and z=50 weight %.

An amount of 54 g of HPVP and 75 g tert-butanol was added to the reaction vessel as a heel charge. The reaction mixture was purged three times with nitrogen while stirring and then heated to 80° C. to 85° C. A pre-mixed feed charge comprising 72 g of EHMA, 54 g of MMA, and tert-butanol was fed in the pump. The feed was started at 70° C. to 80° C. and continued for three hours. The jacket temperature was adjusted to maintain the internal temperature between 80 to 85° C. during the feed. A total amount of 0.9 g of the initial initiator Vazo® 67 was charged in six portions during the feed. After the feed was completed, tert-butanol was used to rinse the feeding line, pump and charge line, and discharged into the reaction vessel. The reaction mixture was maintained on hold for one hour at 85° C. to 85° C. and sampled for analysis by HPLC. An amount of 2.5% by weight of total amount of monomers of chaser initiator Vazo® 67 was charged in six portions. The reaction mixture was maintained on hold for 10 hours at 80° C. to 85° C. The sample was dried under high vacuum at 50° C. to 55° C. In the polymer structure shown, x=30 weight %, y=30 weight % and z=40 weight %.

Example 4

Synthesis of Poly(VP-Co-MMA-Co-EHMA) with VP/MMA/EHMA Weight Ratio of 30:30:40. Three Hour Feed Reaction in Tert-Butanol Solvent Example 5

Synthesis of Poly(VP-Co-TBA-Co-EHMA) with VP/TBA/EHMA Weight Ratio of 20:30:50. Four Hour Feed Reaction in Tert-Butanol Solvent

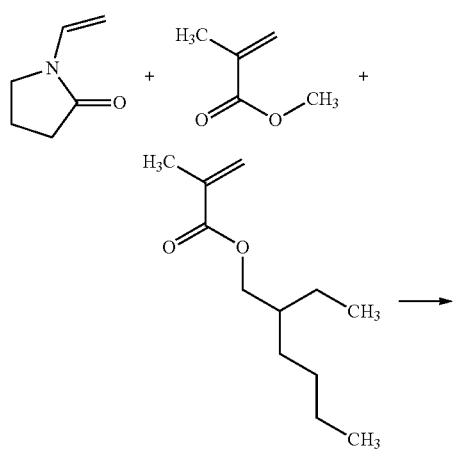

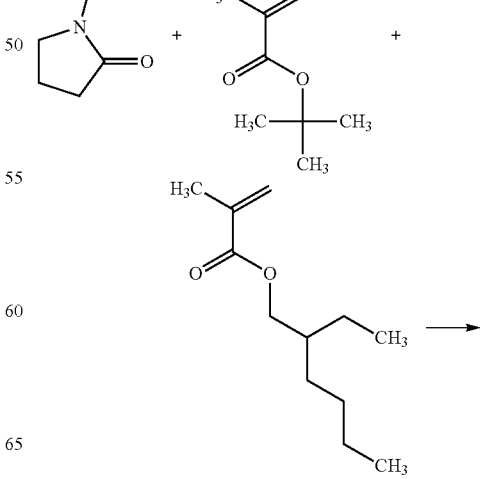

-continued

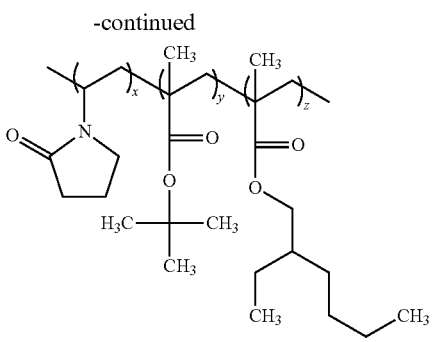

An amount of 36 g of HPVP and 75 g tert-butanol was added to the reaction vessel as a heel charge. The reaction mixture was purged three times with nitrogen while stirring and then heated to 70° C. to 75° C. A pre-mixed feed charge comprising 90 g of EHMA, 54 g of TBA, and tert-butanol was fed in the pump. The feed was started at 70° C. to 80° C. and continued for four hours. The jacket temperature was adjusted to maintain the internal temperature between 70 to 75° C. during the feed. A total amount of 0.9 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 70° C. to 75° C. and sampled for analysis. The temperature was raised to 80° C.-85° C. An amount of 2.5% by weight of total amount of monomers of chaser initiator Luperox® 11 was charged in six portions every hour. The reaction mixture was maintained on hold for 10 hours at 80° C. to 85° C. and sampled for analysis by HPLC. The sample was dried under high vacuum at 50° C. to 55° C. In the polymer structure shown, x=20 weight %, y=30 weight % and z=50 weight %.

Example 6

Synthesis of Poly(VP-Co-MMA-Co-EHMA) with VP/MMA/EHMA Weight Ratio of 20:30:50. Four Hour Feed Reaction in Isopropanol Solvent

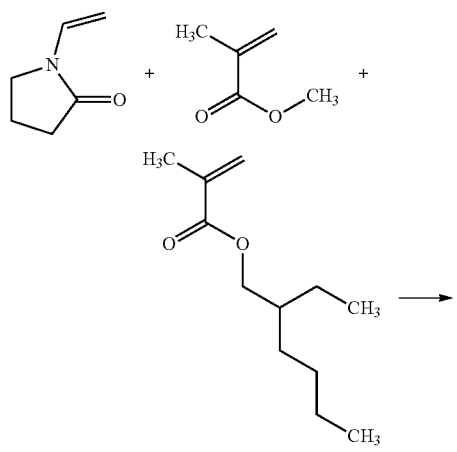

-continued

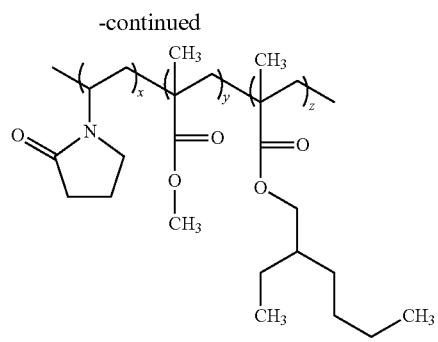

An amount of 36 g of HPVP and 75 g tert-butanol was added to the reaction vessel as a heel charge. The reaction mixture was purged three times with nitrogen while stirring and then heated to 70° C. to 80° C. A pre-mixed feed charge comprising 90 g of EHMA, 54 g of MMA, tert-butanol and 30 g of isopropanol was fed in the pump. The feed was started at 70° C. to 80° C. and continued for four hours. The jacket temperature was adjusted to maintain the internal temperature between 70 to 75° C. during the feed. A total amount of 1.35 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 70° C. to 75° C. and sampled for analysis. The temperature was raised to 80° C.-85° C. An amount of 2.5% by weight of total amount of monomers of chaser initiator Luperox® 11 was charged in six portions every hour. The reaction mixture was maintained on hold for 10 hours at 80° C. to 85° C. and sampled for analysis by HPLC. The sample was dried under high vacuum at 50° C. to 55° C. In the polymer structure shown, x=20 weight %, y=30 weight % and z=50 weight %.

Example 7

Synthesis of Poly(VP-Co-MMA-Co-EHMA) with VP/MMA/EHMA Weight Ratio of 20:50:30. Three Hour Feed Reaction in Tert-Butanol Solvent

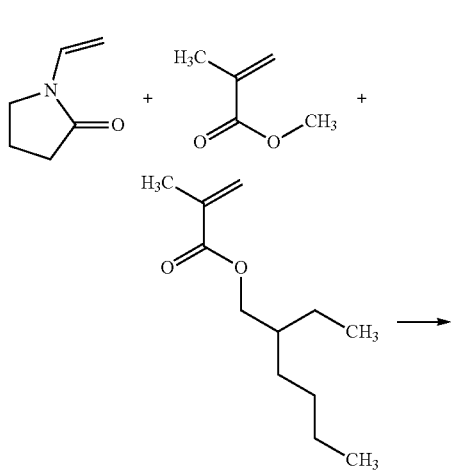

51

-continued

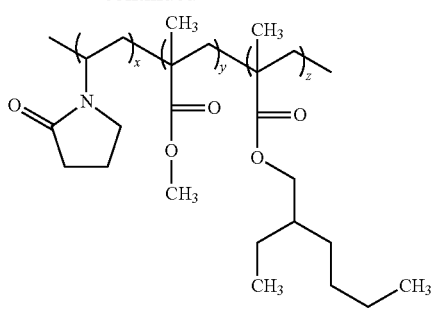

An amount of 36 g of HPVP and 75 g tert-butanol was added to the reaction vessel as a heel charge. The reaction mixture was purged three times with nitrogen while stirring and then heated to 80° C. to 85° C. A pre-mixed feed charge comprising 54 g of EHMA, 90 g of MMA, and tert-butanol was fed in the pump. The feed was started at 70° C. to 80° C. and continued for three hours. The jacket temperature was adjusted to maintain the internal temperature between 80 to 85° C. during the feed. A total amount of 0.9 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 80° C. to 85° C. and sampled for analysis. An amount of 2.5% by weight of total amount of monomers of chaser initiator Luperox® 11 was charged in six portions every hour. The reaction mixture was maintained on hold for 10 hours at 80° C. to 85° C. and sampled for analysis by HPLC. The sample was dried under high vacuum at 50° C. to 55° C. In the polymer structure shown, x=20 weight %, y=50 weight % and z=30 weight %.

Example 8

Synthesis of Poly(VP-Co-MMA-Co-EHMA) with VP/MMA/EHMA Weight Ratio of 20:30:50. Four Hour Feed Reaction in Isopropanol and Tert-Butanol Solvent Combination. 30% Solids Process

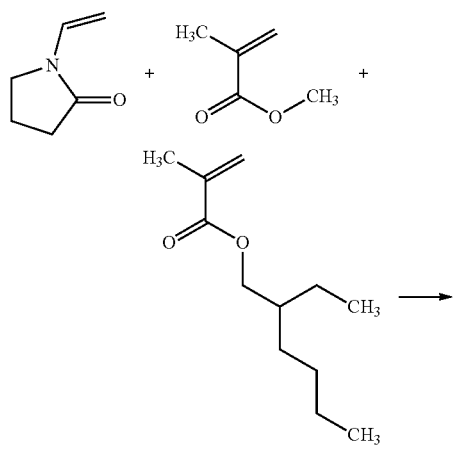

52

-continued

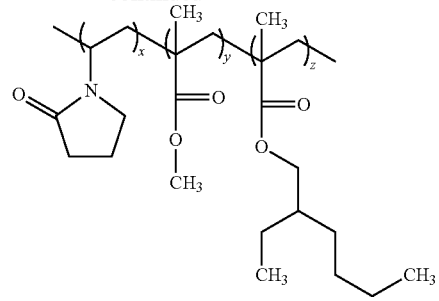

An amount of 36 g of HPVP and 75 g tert-butanol was added to the reaction vessel as a heel charge. The reaction mixture was purged three times with nitrogen while stirring and then heated to 75° C. to 80° C. A pre-mixed feed charge comprising 90 g of EHMA, 54 g of MMA, tert-butanol and 15 g of isopropanol was fed in the pump. The feed was started at 70° C. to 80° C. and continued for four hours. The jacket temperature was adjusted to maintain the internal temperature between 75 to 80° C. during the feed. A total amount of 1.35 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 80° C. to 85° C. and sampled for analysis by HPLC. The temperature was raised to 80° C.-85° C. An amount of 2.5% by weight of total amount of monomers of chaser initiator Luperox® 11 was charged in six portions every hour. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 9

Synthesis of Poly(VP-Co-MMA-Co-EHMA) with VP/MMA/EHMA Weight Ratio of 20:30:50. Four Hour Feed Reaction in Isopropanol and Tert-Butanol Solvent Combination. 40% Solids Process

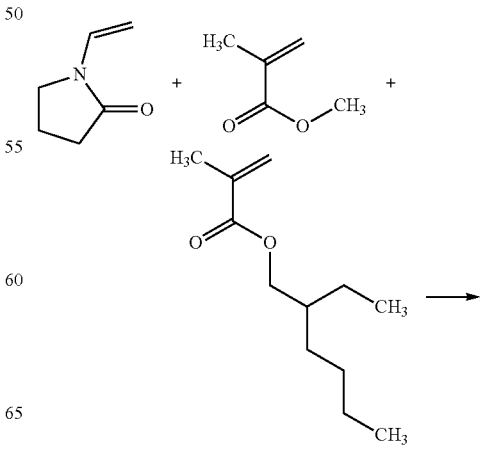

-continued

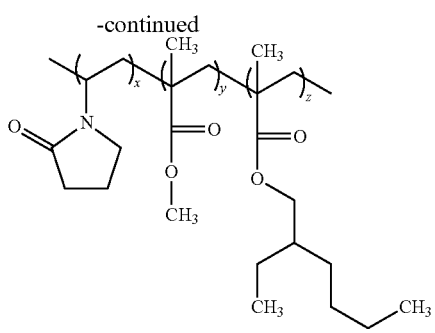

An amount of 36 g of HPVP and 75 g tert-butanol was added to the reaction vessel as a heel charge. The reaction mixture was purged three times with nitrogen while stirring and then heated to 75° C. to 80° C. A pre-mixed feed charge comprising 90 g of EHMA, 54 g of MMA, tert-butanol and 6.5 g of isopropanol was fed in the pump. The feed was started at 70° C. to 80° C. and continued for four hours. The jacket temperature was adjusted to maintain the internal temperature between 75 to 80° C. during the feed. A total amount of 1.35 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 75° C. to 80° C. and sampled for analysis by HPLC. The temperature was raised to 80° C.-85° C. An amount of 2.5% by weight of total amount of monomers of chaser initiator Luperox® 11 was charged in six portions every hour. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 10

Synthesis of Poly(VP-Co-MMA-Co-EHMA) with VP/MMA/EHMA Weight Ratio of 20:30:50. Four Hour Feed Reaction in Isopropanol and Tert-Butanol Solvent Combination. 40% Solids Process. Isopropanol Distilled Off at the End

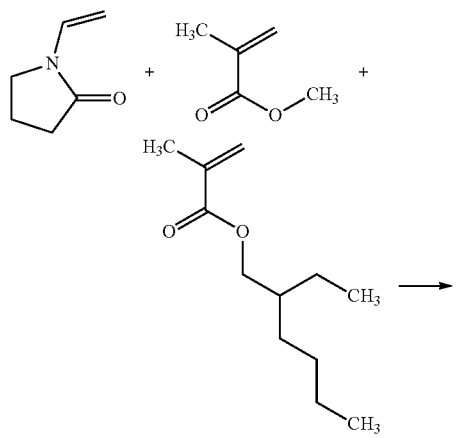

-continued

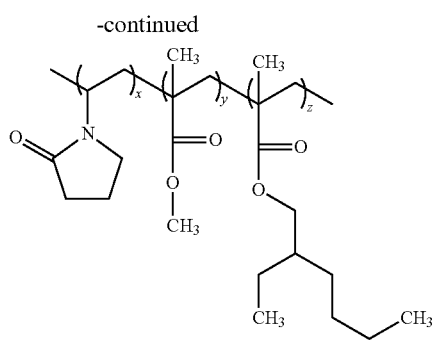

An amount of 36 g of HPVP, 75 g tert-butanol, and 6.5 g of isopropanol was added to the reaction vessel as a heel charge. The reaction mixture was purged three times with nitrogen while stirring and then heated to 75° C. to 80° C. A pre-mixed feed charge comprising 90 g of EHMA, 54 g of MMA, and tert-butanol was fed in the pump. The feed was started at 70° C. to 80° C. and continued for four hours. The jacket temperature was adjusted to maintain the internal temperature between 75 to 80° C. during the feed. A total amount of 1.35 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 75° C. to 80° C. and sampled for analysis by HPLC. The temperature was raised to 80° C.-85° C. and isopropanol removed by atmospheric distillation. An amount of 2.5% by weight of total amount of monomers of chaser initiator Luperox® 11 was charged in six portions. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 11

Synthesis of Poly(VP-Co-MMA-Co-EHMA) with VP/MMA/EHMA Weight Ratio of 20:30:50. Peroxide/Cu Catalyst Process

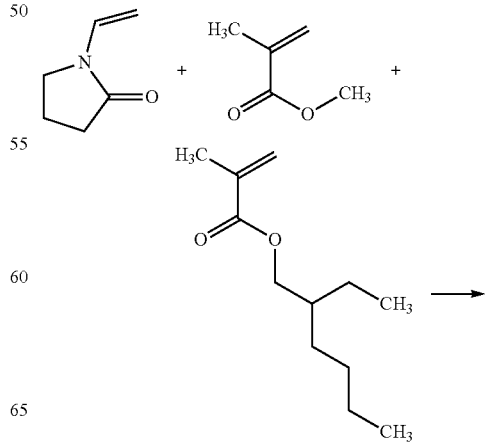

-continued

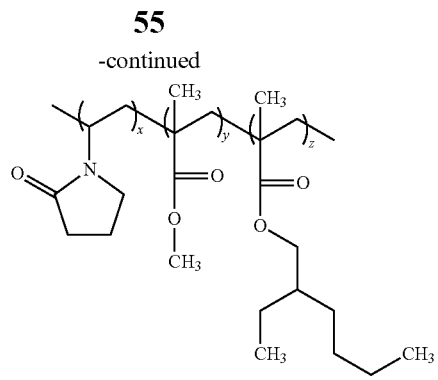

An amount of 36 g of HPVP, 75 g tert-butanol, 23 g of EHMA and 30 g of isopropanol was added to the reaction vessel as a heel charge. The reaction mixture was purged three times with nitrogen while stirring and then heated to 75° C. to 80° C. A pre-mixed feed charge comprising 67 g of EHMA, 54 g of MMA, tert-butanol and isopropanol was fed in the pump. The feed was started at 70° C. to 80° C. and continued for two hours. The jacket temperature was adjusted to maintain the internal temperature between 75 to 80° C. during the feed. $H_2O_2$/Cu catalyst was used as the initial initiator which was charged in six portions during the feed. After the feed was completed, tert-butanol was used to rinse the feeding line, pump and charge line, and discharged into the reaction vessel. The reaction mixture was maintained on hold for one hour at 75° C. to 80° C. and sampled for analysis by HPLC. The temperature was raised to 80° C.-85° C. An amount of 2.5% by weight of total amount of monomers of chaser initiator $H_2O_2$/Cu catalyst was charged in six portions. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 12

Synthesis of Poly(VP-Co-MMA-Co-EHMA) with VP/MMA/EHMA Weight Ratio of 20:30:50. EHMA Added Partly in Heel in Tert-Butanol Solvent

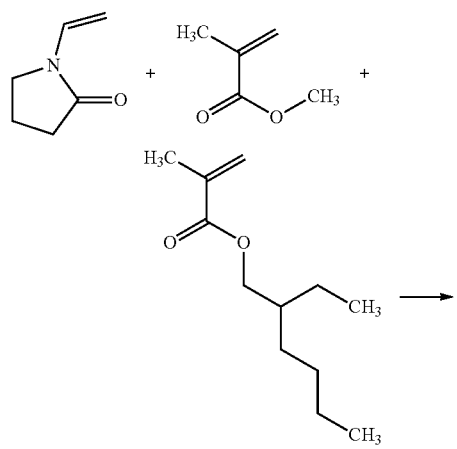

-continued

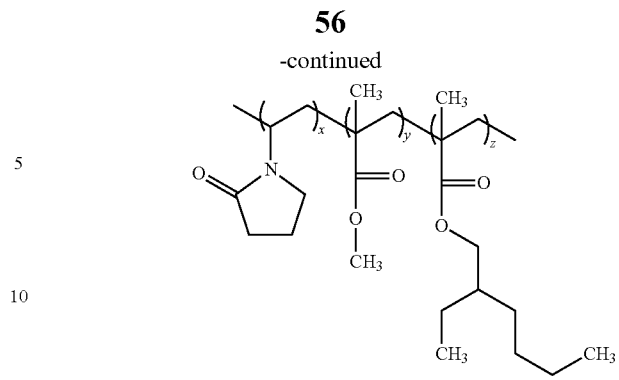

An amount of 36 g of HPVP, 75 g tert-butanol, and 23 g of EHMA was added to the reaction vessel as a heel charge. The reaction mixture was purged three times with nitrogen while stirring and then heated to 75° C. to 80° C. A pre-mixed feed charge comprising 67 g of EHMA, 54 g of MMA, and tert-butanol was fed in the pump. The feed was started at 70° C. to 80° C. and continued for two hours. The jacket temperature was adjusted to maintain the internal temperature between 80 to 85° C. during the feed. A total amount of 1.35 g of the initial initiator Luperox® 11 was charged in six portions during the feed. After the feed was completed, tert-butanol was used to rinse the feeding line, pump and charge line, and discharged into the reaction vessel. The reaction mixture was maintained on hold for one hour at 80° C. to 85° C. and sampled for analysis by HPLC. An amount of 1.5% by weight of total amount of monomers of chaser initiator Luperox® 11 was charged in three portions in three hours. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 13

Synthesis of Poly(VP-Co-MMA-Co-EHMA) with VP/MMA/EHMA Weight Ratio of 20:30:50. EHMA Added Partly in Heel in Tert-Butanol and Isopropanol Solvent Combination

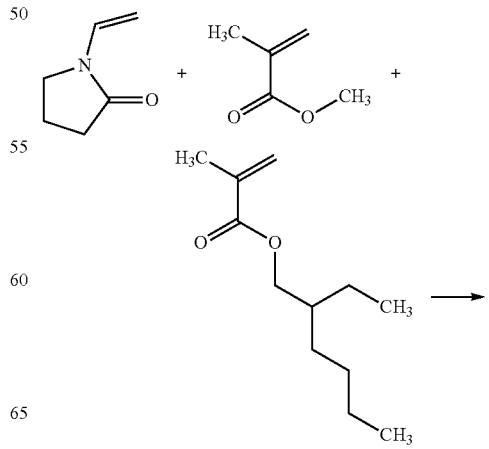

-continued

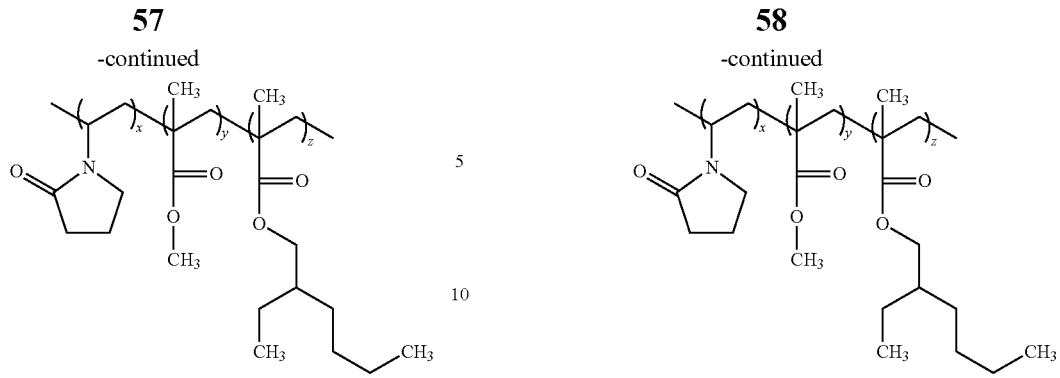

An amount of 36 g of HPVP, 77 g tert-butanol, 45 g of EHMA, and 33 g of isopropanol was added to the reaction vessel as a heel charge. The reaction mixture was purged three times with nitrogen while stirring and then heated to 70° C. to 75° C. A pre-mixed feed charge comprising 45 g of EHMA, 54 g of MMA, tert-butanol, and isopropanol was fed in the pump. The feed was started at 70° C. to 75° C. and continued for two hours. The jacket temperature was adjusted to maintain the internal temperature between 75 to 80° C. during the feed. A total amount of 1.35 g of the initial initiator Luperox® 11 was charged in three portions during the feed. After the feed was completed, tert-butanol was used to rinse the feeding line, pump and charge line, and discharged into the reaction vessel. The reaction mixture was maintained on hold for one hour at 75° C. to 80° C. and sampled for analysis by HPLC. The temperature was raised to 120° C.-130° C. An amount of 1.5% by weight of total amount of monomers of chaser initiator Luperox® 101 was charged in six portions. The reaction mixture was maintained on hold for six hours at 120° C. to 130° C. The sample was dried under high vacuum at 50° C. to 55° C. In the polymer structure shown, x=20 weight %, y=30 weight % and z=50 weight %.

An amount of 36 g of HPVP, 38 g n-heptane, 36 g of EHMA, and 0.5 g of Vazo® 67 was added to the reaction vessel as a heel charge. The reaction mixture was purged three times with nitrogen while stirring and then heated to 80° C. to 85° C. A pre-mixed feed charge comprising 54 g of EHMA, 54 g of MMA, and n-heptane was fed in the pump. The feed was started at 70° C. to 75° C. and continued for two hours. The jacket temperature was adjusted to maintain the internal temperature between 75 to 80° C. during the feed. After the feed was completed, n-heptane was used to rinse the feeding line, pump and charge line, and discharged into the reaction vessel. The reaction mixture was maintained on hold for one hour at 75° C. to 80° C. and sampled for analysis by HPLC. The temperature was raised to 85° C.-90° C. An amount of 2.0% by weight of total amount of monomers of chaser initiator Luperox® 121 was charged in four portions. The reaction mixture was maintained on hold for 10 hours at 90° C. The sample was dried under high vacuum at 50° C. to 55° C. In the polymer structure shown, x=20 weight %, y=30 weight % and z=50 weight %.

Example 14

Synthesis of Poly(VP-Co-MMA-Co-EHMA) with VP/MMA/EHMA Weight Ratio of 20:30:50. EHMA Added Partly in Heel in n-Heptane Solvent Example 15

Synthesis of Poly(VP-Co-MMA-Co-EHMA) with VP/MMA/EHMA Weight Ratio of 20:30:50. EHMA Added Partly in Heel in Ceraphyl® 230

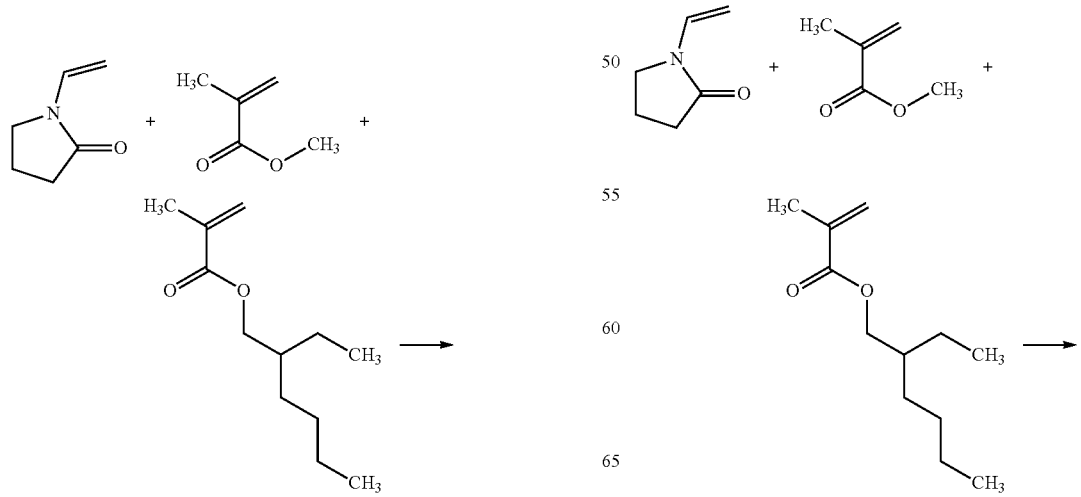

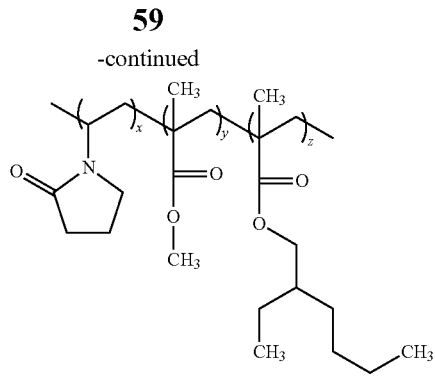

An amount of 36 g of HPVP, 39 g Ceraphyl® 230, 36 g of EHMA, and 0.9 g of Luperox® 11 was added to the reaction vessel as a heel charge. The reaction mixture was purged three times with nitrogen while stirring and then heated to 80° C. to 85° C. A pre-mixed feed charge comprising 54 g of EHMA, 54 g of MMA, and Ceraphyl® 230 was fed in the pump. The feed was started at 70° C. to 75° C. and continued for two hours. The jacket temperature was adjusted to maintain the internal temperature between 75 to 80° C. during the feed. After the feed was completed, Ceraphyl® 230 was used to rinse the feeding line, pump and charge line, and discharged into the reaction vessel. The reaction mixture was maintained on hold for one hour and sampled for analysis by HPLC. An amount of 2.0% by weight of total amount of monomers of chaser initiator Luperox® 11 was charged in four portions. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Example 16

Synthesis of Poly(VP-Co-MMA-Co-EHMA) with VP/MMA/EHMA Weight Ratio of 20:30:50. EHMA not Added in Heel. Ceraphyl® 230 Solvent

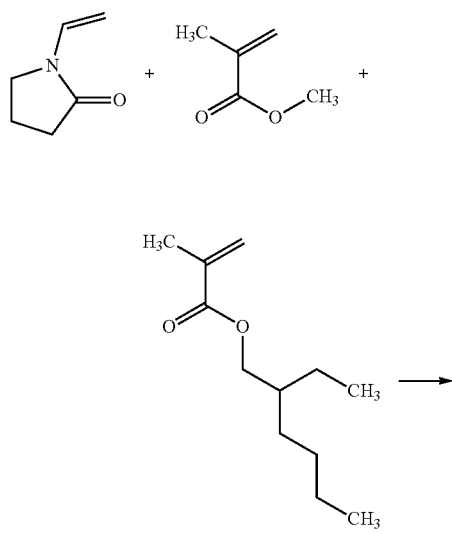

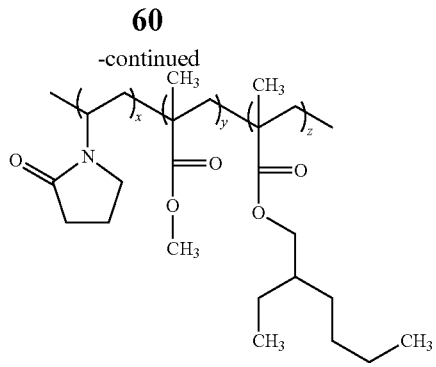

An amount of 36 g of HPVP, 75 g Ceraphyl® 230 and 0.9 g of Luperox® 11 was added to the reaction vessel as a heel charge. The reaction mixture was purged three times with nitrogen while stirring and then heated to 80° C. to 85° C. A pre-mixed feed charge comprising 90 g of EHMA, 54 g of MMA, and Ceraphyl® 230 was fed in the pump. The feed was started at 70° C. to 75° C. and continued for two hours. The jacket temperature was adjusted to maintain the internal temperature between 75 to 80° C. during the feed. After the feed was completed, Ceraphyl® 230 was used to rinse the feeding line, pump and charge line, and discharged into the reaction vessel. The reaction mixture was maintained on hold for one hour and sampled for analysis by HPLC. An amount of 2.0% by weight of total amount of monomers of chaser initiator Luperox® 11 was charged in four portions. The reaction mixture was maintained on hold for 10 hours at 80° C. to 85° C. The sample was dried under high vacuum at 50° C. to 55° C. In the polymer structure shown, x=20 weight %, y=30 weight % and z=50 weight %.

Sun Care Application Data

The sun care formulations comprising polymers according to the invention were tested for water resistance using an in-vitro method, the procedure of which is provided below:
In-Vitro Water Resistance
(1) VITRO-SKIN® (VS) was cut into 3.0 cm×4.0 cm strips and mounted in place in a 35 mm slide holder.
(2) Four slides were made for each test product.
(3) One slide was made for the blank, to obtain the baseline and zero readings.
(4) The slides were then placed into a hydration chamber for 12-14 hours to allow the VS to hydrate. The relative humidity of the chamber was maintained by an 18% w/w glycerin solution.
(5) An amount of 6 to 7 mg of the test product was applied to each strip of VS. The slide was then placed back in the humidity chamber for 20 minutes to allow for coalescence of the test product.
(6) The initial UV absorbance of each slide was measured with a UV-Visible spectrophotometer (Cary 300 Series) in the wavelength range of 290-400 nm.
(7) Two readings were taken for each slide—one from each end.
(8) The slides were then immersed in a 25° C. water bath, with circulation of 90 rpm for 80 minutes. The slides were then removed and allowed to air dry for 15 minutes.
(9) The slides were equilibrated in the humidity chamber for 120 minutes, and the absorbance post immersion was calculated.
(10) The initial and post absorbance data was saved as a spreadsheet and exported to an Excel spreadsheet.

(11) Area under the curve (sum of the y value) from 290-400 nm was calculated for each reading. This was done for both initial readings and post immersion readings.
(12) The percent water resistance was calculated from the following equation:

Percent Water Resistance=(Absorbance post immersion/Initial Absorbance)×100.

(13) The average value of four slides gave the final percent water resistance.

Sun Care Emulsion I

TABLE 1

List of components of Sun Care Emulsion I

| Phase | Ingredient | Trade Name (manufacturer) | Composition, % w/w |
|---|---|---|---|
| A | Water | | 52.65 |
| | Phenoxyethanol (and) Methylparaben (and) Ethylparaben (and) Propylparaben | Rokonsal ™/ LiquaPar ™ MEP preservative (Ashland Inc.) | 1.00 |
| | Triethanolamine | Triethanolamine (Dow) | 0.15 |
| | Acrylic Acid/VP Crosspolymer | UltraThix ™ P-100 polymer (Ashland) | 0.40 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 8.00 |
| | Octocrylene | Escalol ™ 597 UV filter (Ashland) | 5.00 |
| | Benzopheneone -3 | Escalol ™ 567 UV filter (Ashland) | 6.00 |
| | Glyceryl Stearate (and) PEG-100 Stearate | Arlacel ™ 165 (Croda) | 4.00 |
| | Diisopropyl Adipate | Ceraphyl ™ 230 ester (Ashland) | 5.50 |
| | C12-15 Alkyl Lactate | Ceraphyl ™ 41 ester (Ashland) | 2.50 |
| | Glyceryl Dilaurate | Emulsynt ™ GDL emulsifier (Ashland) | 0.50 |
| | Stearyl Alcohol | | 1.00 |
| C | Glycerin (and) Glyceryl Polyacrylate | Lubrajel ™ II-XD (Ashland) | 1.00 |
| | Cyclopentasiloxane | Si-Tec CM040 | 3.00 |
| D | Phenoxyethanol (and) Methylisothiozolinone | Optiphen ™ MIT Ultra (Ashland) | 0.30 |
| | Total | | 99.0 |

An amount of 1.0 g of the polymer prepared according to Example 1 was added to Phase B of Sun Care Emulsion I and the resulting emulsion was tested for water resistance. FIG. 1 shows the percent water resistance value of the emulsion comprising polymer of Example 1 in comparison with various commercially available sun care products.

Sun Care Emulsion II

TABLE 2

List of components of Sun Care Emulsion II

| Phase | Ingredient | Trade Name (manufacturer) | Composition, % w/w |
|---|---|---|---|
| A | Water | | 51.60 |
| | Glycerin | Glycerin (Ruger) | 1.00 |
| | Phenoxyethanol (and) Methylparaben (and) Ethylparaben (and) Propylparaben | LiquaPar ™ MEP preservative (Ashland) | 1.00 |
| | Carbomer | Carbomer ™ 980 (Ashland) | 0.30 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 8.00 |
| | Octocrylene | Escalol ™ 597 UV filter (Ashland) | 5.00 |
| | Benzopheneone -3 | Escalol ™ 567 UV filter (Ashland) | 6.00 |
| | Glyceryl Stearate (and) PEG-100 Stearate | Arlacel ™ 165 (Croda) | 4.00 |
| | Diisopropyl Adipate | Ceraphyl ™ 230 ester (Ashland) | 5.50 |
| | C12-15 Alkyl Lactate | Ceraphyl ™ 41 ester (Ashland) | 2.50 |
| | Glyceryl Dilaurate | Emulsynt ™ GDL emulsifier (Ashland) | 0.50 |
| | Stearyl Alcohol | | 1.00 |
| | Triethanolamine | Triethanolamine (Dow) | 0.30 |
| C | Glycerin (and) Glyceryl Polyacrylate | Lubrajel ™ II-XD (Ashland) | 1.00 |
| | Cyclopentasiloxane | Si-Tec CM040 | 3.00 |
| D | Phenoxyethanol (and) Methylisothiozolinone | Optiphen ™ MIT Ultra (Ashland) | 0.30 |
| | Total | | 99.0 |

Figure 2:
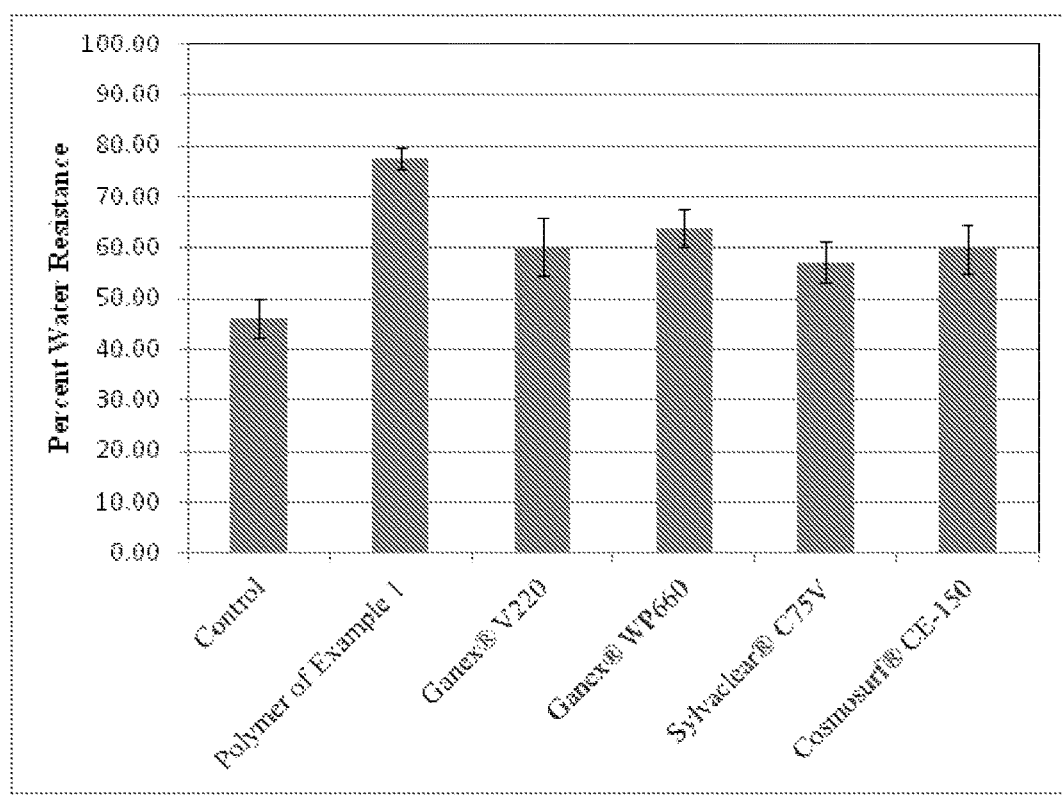

An amount of 1.0 g of the polymer prepared according to Example 1 was added to Phase B of Sun Care Emulsion II and the resulting emulsion was tested for water resistance. FIG. 2 shows the percent water resistance of the emulsion comprising polymer of Example 1 in comparison with various commercially available sun care products.

Sun Care Emulsion III

TABLE 3

List of components of Sun Care Emulsion III

| Phase | Ingredient | Trade Name (manufacturer) | Composition, % w/w |
|---|---|---|---|
| A | Water | | 55.70 |
| | Glycerin | Glycerin (Ruger) | 2.00 |
| | Xanthan Gum | | 0.50 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 8.00 |
| | Octocrylene | Escalol ™ 597 UV filter (Ashland) | 5.00 |
| | Benzopheneone -3 | Escalol ™ 567 UV filter (Ashland) | 6.00 |
| | Glyceryl Stearate (and) PEG-100 Stearate | Arlacel ™ 165 (Croda) | 4.00 |
| | Diisopropyl Adipate | Ceraphyl ™ 230 ester (Ashland) | 5.50 |
| | C12-15 Alkyl Lactate | Ceraphyl ™ 41 ester (Ashland) | 2.50 |

TABLE 3-continued

List of components of Sun Care Emulsion III

| Phase | Ingredient | Trade Name (manufacturer) | Composition, % w/w |
|---|---|---|---|
| C | Glyceryl Dilaurate | Emulsynt ™ GDL emulsifier (Ashland) | 0.50 |
| | Stearyl Alcohol | | 1.00 |
| | Phenoxyethanol (and) Methylisothiozolinone | Optiphen ™ MIT Ultra (Ashland) | 0.30 |
| | Total | | 99.0 |

Figure 3:
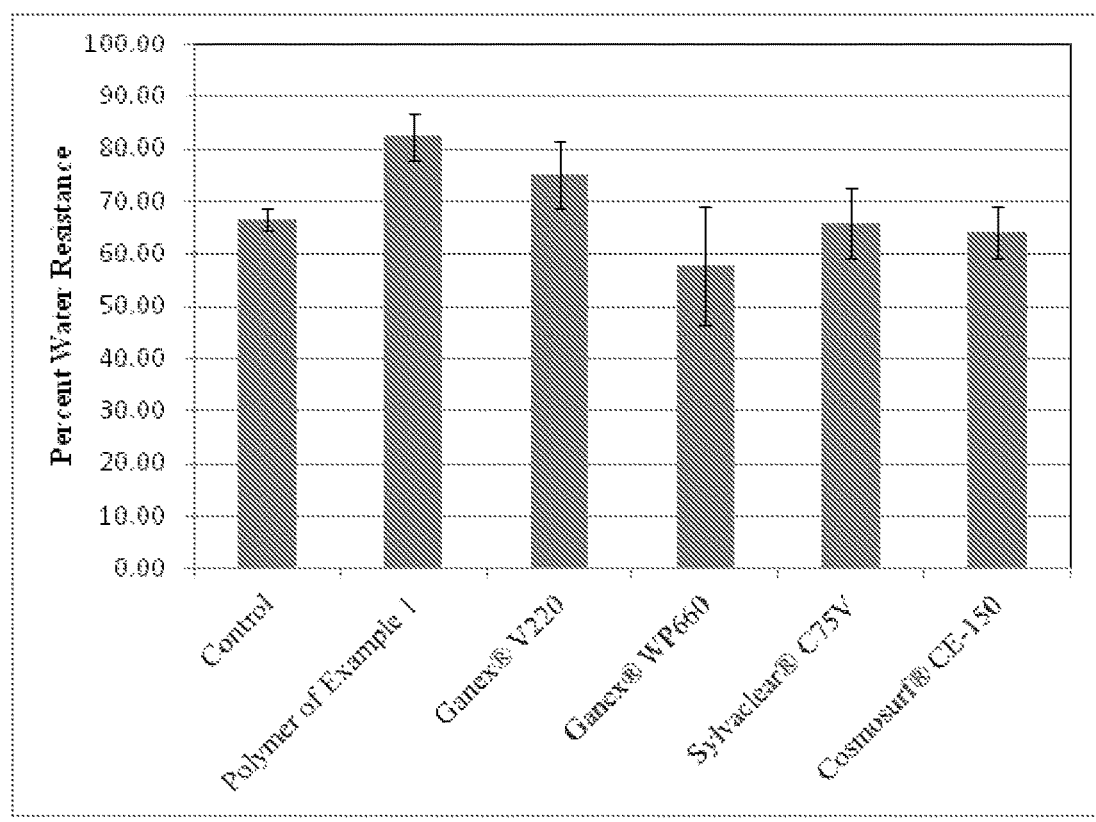

An amount of 1.0 g of the polymer prepared according to Example 1 was added to Phase B of Sun Care Emulsion III and the resulting emulsion was tested for water resistance. FIG. 3 shows the percent water resistance of the emulsion comprising polymer of Example 1 in comparison with various commercially available sun care products.

Anhydrous Formulation

TABLE 4

List of components of Anhydrous Formulation

| Phase | Ingredient | Trade Name (manufacturer) | Composition, % w/w |
|---|---|---|---|
| A | Ethanol | | 66.00 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 10.00 |
| | Octocrylene | Escalol ™ 597 UV filter (Ashland) | 10.00 |
| | Benzopheneone -3 | Escalol ™ 567 UV filter (Ashland) | 5.00 |
| | Total | | 99.0 |

Figure 4:
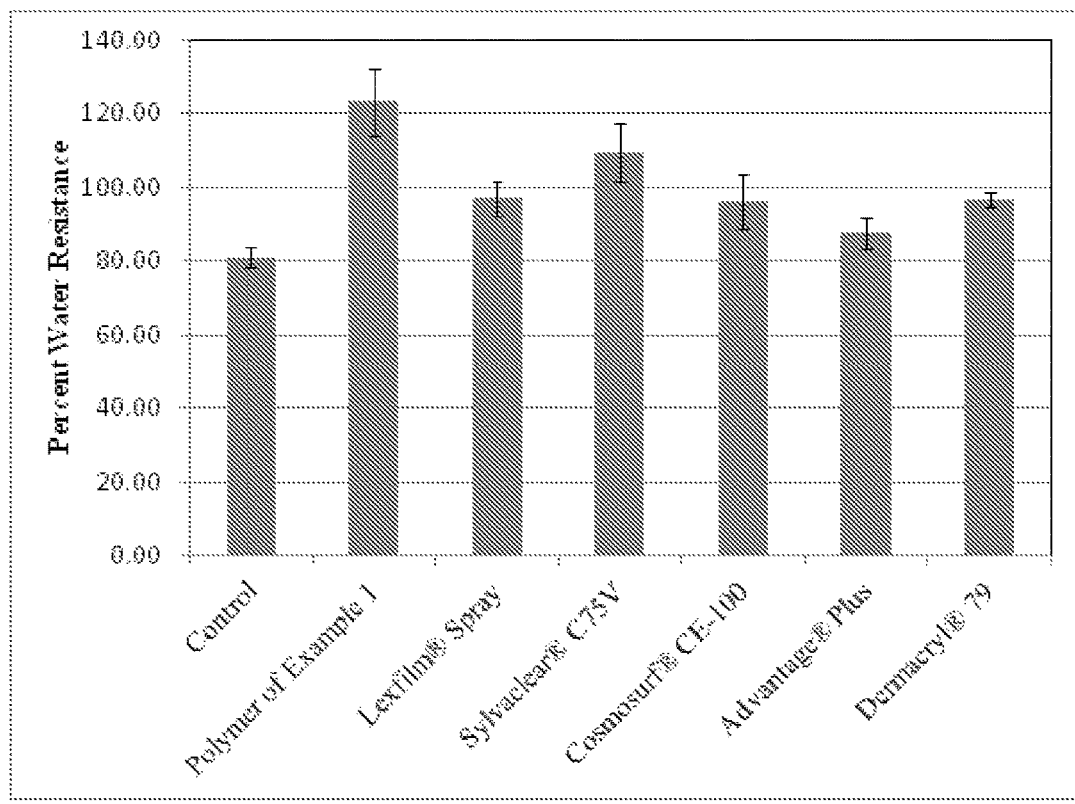
Figure 5:
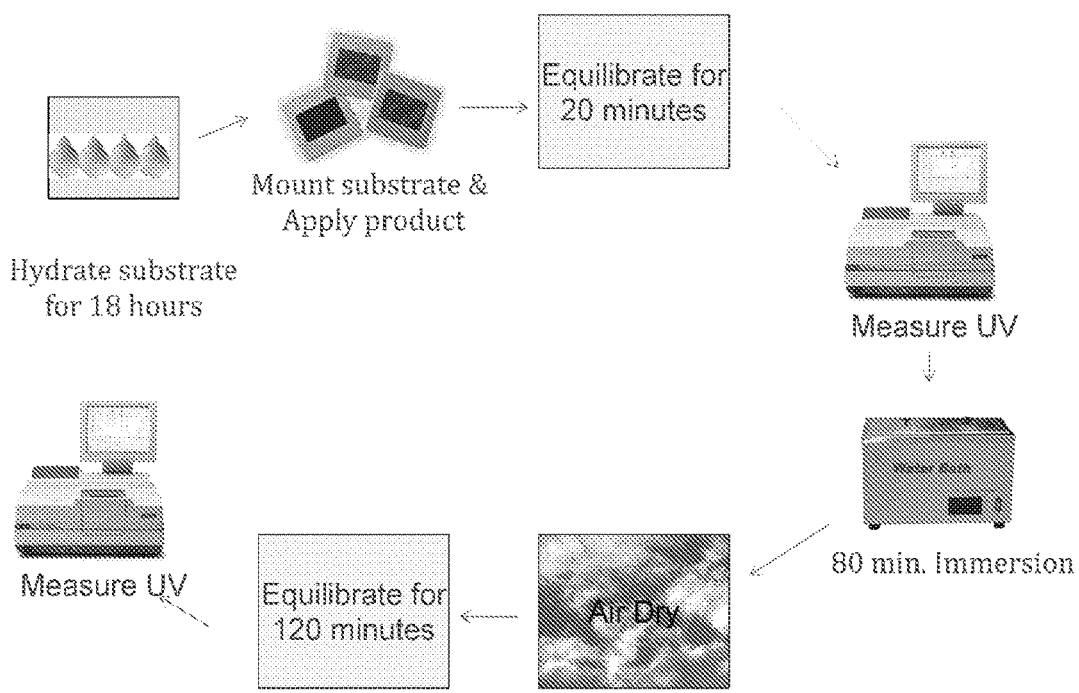
FIG. 5 depicts the in-vitro water resistance test method.

An amount of 1.0 g of the polymer prepared according to Example 1 was added to Phase B of the Anhydrous Formulation and the resulting formulation was tested for water resistance. FIG. 4 shows the percent water resistance of the Anhydrous Formulation comprising polymer of Example 1 in comparison with various commercially available sun care products.

All references including patent applications and publication cited herein are incorporated herein by reference in their entirety and for all purpose to the same extent as if each individual publication or patent or patent application was specifically and individually indicated to be incorporated by reference in its entirety for all purposes. Many modifications and variations of the presently disclosed and claimed inventive concept(s) can be made without departing from its spirit and scope, as will be apparent to those skilled in the art.

What is claimed is:

1. A personal care composition comprising a polymer comprising repeating units derived from:
   (a) from 16% by weight to about 35% by weight of said polymer of at least one N-vinyl lactam monomer;
   (b) at least one monomer selected from the group consisting of functionalized and unfunctionalized $C_1$-$C_6$ alkyl (meth)acrylates, $C_1$-$C_6$ alkyl (meth)acrylamides and combinations thereof; and
   (c) at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof; wherein said polymer has a glass transition temperature of greater than about 45° C.

2. The personal care composition according to claim 1 wherein said personal care composition is a sun care composition, a face care composition, a lip care composition, an eye care composition, a skin care composition, an after-sun composition, a body care composition, a nail care composition, an anti-aging composition, an insect repellant, an oral care composition, a deodorant composition, a hair care composition, a conditioning composition, a color cosmetic composition, a color-protection composition, a self-tanning composition, or a foot care composition.

3. The personal care composition according to claim 2 wherein said personal care composition is a sun care composition.

4. The personal care composition according to claim 3 wherein said sun care composition is a water-resistant sun care composition.

5. The personal care composition according to claim 4 wherein said water-resistant sun care composition further comprises at least one UV active.

6. The personal care composition according to claim 5 wherein said water-resistant sun care composition further comprises at least one additive selected from the group consisting of secondary polymers for improving water-resistance, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, pharmaceutically or dermatologically or cosmetically acceptable excipients, and combinations thereof.

7. The personal care composition according to claim 4 wherein said water-resistant sun care composition is in the form of an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous gel, an aqueous gel, an alcoholic solution or a hydro-alcoholic solution.

8. A method for protecting a keratinous substrate from UV radiation comprising applying onto said substrate a water resistant sun care composition comprising:
   (a) a polymer comprising repeating units derived from: from 16% by weight to about 35% by weight of said polymer of at least one N-vinyl lactam monomer; at least one monomer selected from the group consisting of functionalized and unfunctionalized $C_1$-$C_6$ alkyl (meth)acrylates, $C_1$-$C_6$ alkyl (meth)acrylamides and combinations thereof; and at least one monomer selected from the group consisting of functionalized and unfunctionalized $C_8$-$C_{30}$ branched alkyl (meth)acrylates, $C_8$-$C_{30}$ branched alkyl (meth)acrylamides, and combinations thereof, wherein said polymer has a glass transition temperature of greater than about 45° C.; and
   (b) at least one UV active.

* * * * *